(12) United States Patent
Holloway

(10) Patent No.: US 6,775,622 B1
(45) Date of Patent: Aug. 10, 2004

(54) METHOD AND SYSTEM FOR DETECTING NEAR IDENTITIES IN LARGE DNA DATABASES

(75) Inventor: James L. Holloway, Seattle, WA (US)

(73) Assignee: ZymoGenetics, Inc., Seattle, WA (US)

(*) Notice: Subject to any disclaimer, the term of this patent is extended or adjusted under 35 U.S.C. 154(b) by 114 days.

(21) Appl. No.: 09/772,813

(22) Filed: Jan. 30, 2001

Related U.S. Application Data

(60) Provisional application No. 60/179,309, filed on Jan. 31, 2000.

(51) Int. Cl.[7] ............................................. G06F 19/00
(52) U.S. Cl. ........................................................ 702/20
(58) Field of Search .......................................... 702/20

*Primary Examiner*—John S. Brusca
(74) *Attorney, Agent, or Firm*—Shelby J. Walker

(57) ABSTRACT

The present invention provides a solution to the needs described above through a system and method for efficiently detecting near identities in large DNA databases. The system and method disclosed herein make use of an algorithm used to construct and maintain unique DNA databases wherein the unique database contains no two DNA sequences such that one is nearly identical to a region of the other. The system and method are applicable to problems such as an all against all comparison of all the DNA sequences in a large DNA database, clustering and assembling ESTs into the cDNAs that generated the ESTs, mapping assembled ESTs onto genomic sequence, mapping cDNAs onto genomic sequences and locating alternately spliced cDNAs.

35 Claims, 13 Drawing Sheets

200 Typical General Purpose Computer/

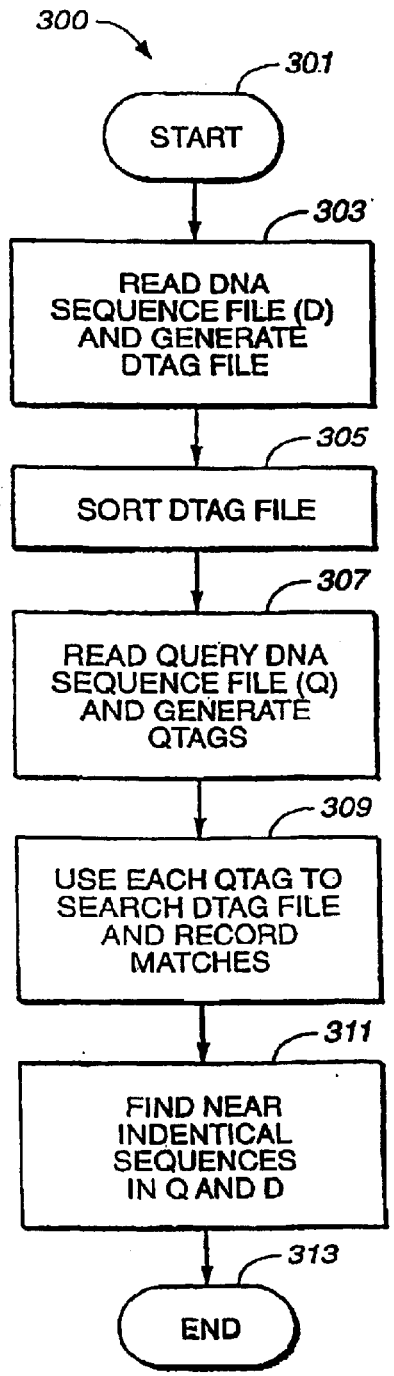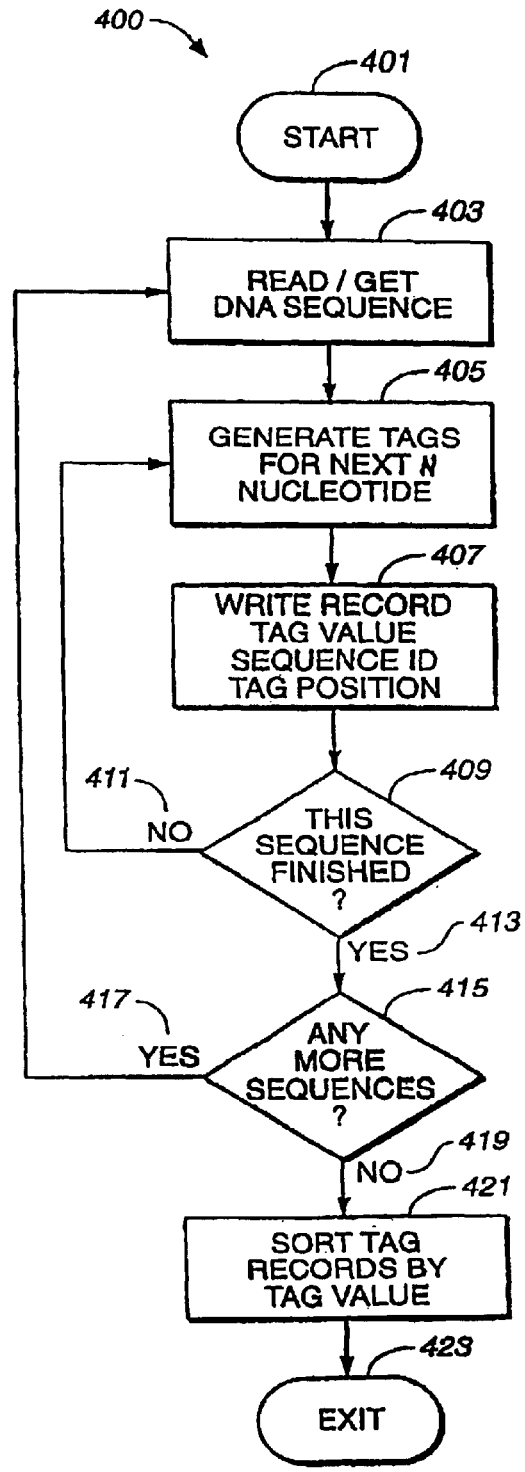
FIG._3
FIG._4

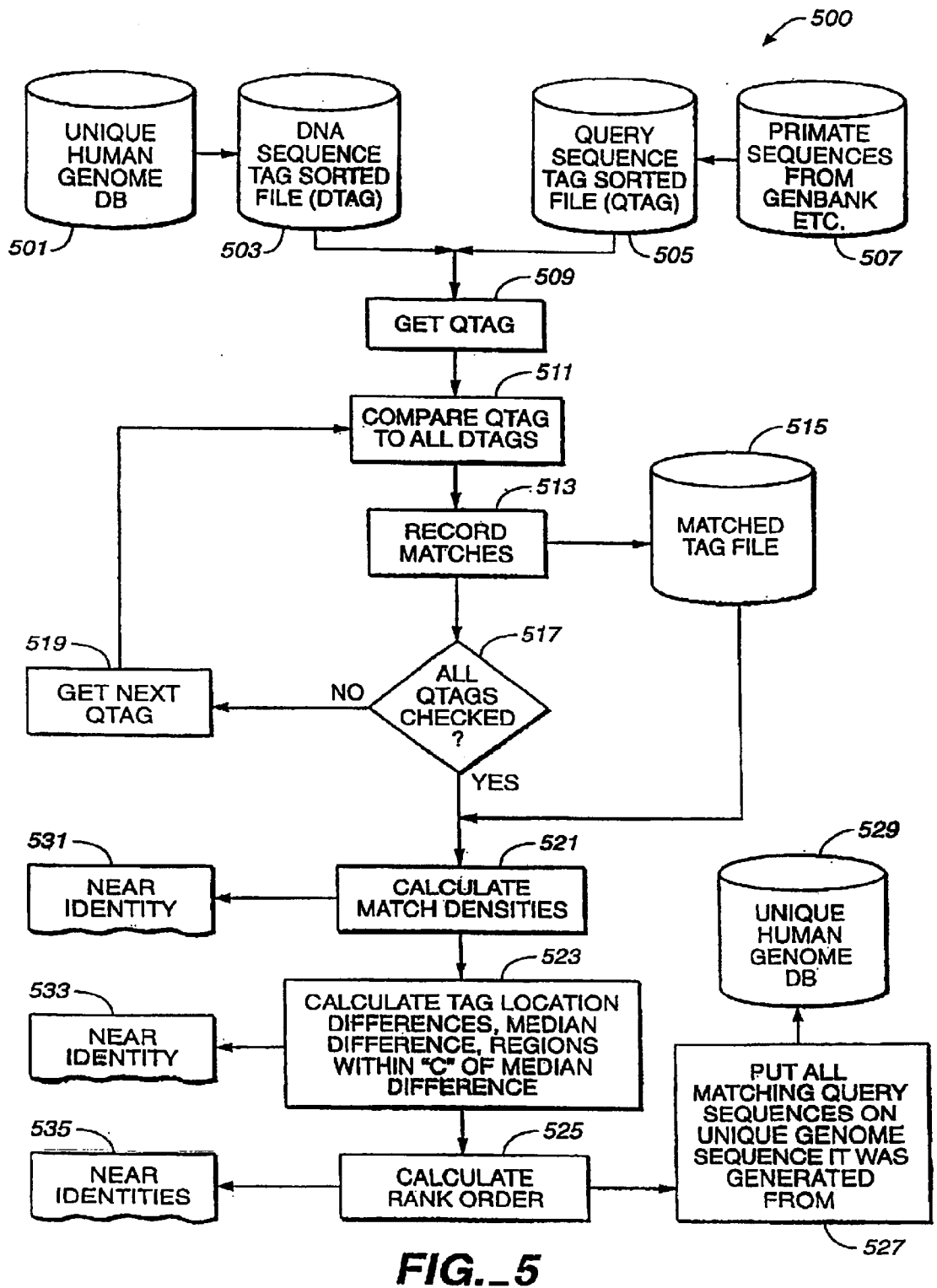
FIG._5

*Fig. 6A.*

```
      swiss-prot like format:
             603    605
601 —ID   Z0;  753000 NA.
607 —AC   Z0;
          609
611 —DR   /vols/pdata/na/genomic/GEN_HUMAN.NDB; AC003656;
          753000 0 753000      Z0 753000 0 753000       249 1.00
          0.00 3847 9331104677
                               619                              617
613 —DR   /vols/pdata/na/genomic/GEN_HUMAN.NDB; AQ474914;
625 —350 1 289   Z0 753000 557888 558176 9 -1.00 0.00 262
                           627              623      629     631  635
636 —9331104677
          DR   /vols/pdata/na/genomic/GEN_HUMAN.NDB; AQ484430;
          346 6 299   Z0 753000 265056 265344 5 -1.00 1.00 262
          9331104677                                          633
          DR   /vols/pdata/na/genomic/GEN_HUMAN.NDB; G34630; 500
          41 457   Z0 753000 660416 660832 14 -1.00 0.00 262
          9331104677
          DR   /vols/pdata/na/genomic/GEN_HUMAN.NDB; AQ197006;
          551 41 489 Z0 753000 323936 324384 15 -1.00 0.00 262
          9331104677
```

```
DR   /vols/pdata/na/genomic/GEN_HUMAN.NDB; G34621; 480
2 418   ZO 753000 -286656 -286240        14 -1.00 0.00
390 9331104467
DR   /vols/pdata/na/genomic/GEN_HUMAN.NDB; G34622; 480
6 422   ZO 753000 276448 276864  14 -1.00 0.00 262
9331104467
DR   /vols/pdata/na/genomic/GEN_HUMAN.NDB; G34623; 480
3 419   ZO 753000 -409472 -409056        14 -1.00 0.00
390 9331104467
DR   /vols/pdata/na/genomic/GEN_HUMAN.NDB; G34625; 480
28 444  ZO 753000 16448 16864    14 -1.00 0.00 2310
9331104467
DR   /vols/pdata/na/genomic/GEN_HUMAN.NDB; G34628; 480
12 429  ZO 753000 491296 491712 12 -1.00 0.30 262
9331104467
DR   /vols/pdata/na/genomic/GEN_HUMAN.NDB; AQ530866;
629 17 593 ZO 753000 379104 379680 12 -1.00 0.00 262
9331104467
```

*Fig. 6B.*

```
DR  /vols/pdata/na/genomic/GEN_HUMAN.NDB; AQ284594;
656 11 587 Z0 753000 368416 368992 18 -1.00 0.00 262
933110467
DR  /vols/pdata/na/genomic/GEN_HUMAN.NDB; AQ055000;
637 26 569 Z0 753000 675232 675776 17 -1.00 0.15 262
933110467
DR  /vols/pdata/na/genomic/GEN_HUMAN.NDB; G34769; 213
8 168    Z0 753000 -136224 -136064     6 -1.00 0.00
390 933110467
DR  /vols/pdata/na/genomic/GEN_HUMAN.NDB; G20808; 213
8 168    Z0 753000 -136224 -136064     6 -1.00 0.00
390 933110467
DR  /vols/pdata/na/genomic/GEN_HUMAN.NDB; AQ582860;
523 27 443 Z0 753000 -3706656 -3706240      14 -1.00
0.00 390 933110467
DR  /vols/pdata/na/genomic/GEN_HUMAN.NDB; HSMC12B05; -
214 16 176     Z0 753000 -216640 -216480      6
1.00 0.00 390 933110467
```

Fig. 6C.

```
DR    /vols/pdata/na/genomic/GEN_HUMAN.NDB; G372258;  389
20  340    Z0 753000 -169280 -168960       11 -1.00  0.00
390 933110467
DR    /vols/pdata/na/genomic/GEN_HUMAN.NDB; B69654;   582
43  491    Z0 753000  226048  226496  13 -1.00  0.00  262
933110467
DR
/home/disc/holloway/software/genomic_uniq/data/gen_072
9.fasta; AQ746139;  841  59  731       Z0 753000 -215936
-215264        15 -1.00  0.00 390 933286163DR
/home/disc/holloway/software/genomic_uniq/data/gen_072
9.fasta; AQ729823;  445  42  395       Z0 753000  104448
104800  10 -1.00  0.38 262 933286163
```

Fig. 6D.

637 — SQ    SEQUENCE length 753000 NA;
639 — agcgtgtgtcagtgcgaaacccgagataagctatcacgtaatcgccaagtgtcgttaattcaccata
gttcacatttaaatacccacgtatcatgtataattaaacattggccctccactgagtacgtgtgta
gcgcttagtgggcgacacgcatgggcgcaagcaggaaaagtttaaaagaaggccgccctagtgtcacc
cgacaaagcctgacaaacccgaattgcactcgcaattcacggcatacggtcatttagcgtct
atcaccgtagtggtatattgtaatccatcgatacggcgtttggtttgtcttacggttagtaaggggcgtg
cggacgatattaggtgcaaagtcttcaagcatcacacccagaaaagttaccaaggttgtcgcgtgaaagt
taccaagcctcacacgtgaaaagttaccaatcctgtcgcgtgaaaagcatcacacgtgaaaa
gttaccaatcatgtcgcgtgaaaagttaccaagcatcacacgtgaaaagttaccaagcaactcgcgtg
aaagttaccaagcatcacacgtgaaaagttaccaagaagttaccaagcaactcgcgtgaa
aaagttaccaagcattacactttctcttacaagaatttaagaaaatcgttccacccgccatcca
tcatcttcaaacctcgtttgcccgggcactcgtattatgcggggtggcgggctcgcggcacaagagagc
.... (SEQ ID NO: 9)

Fig. 6E.

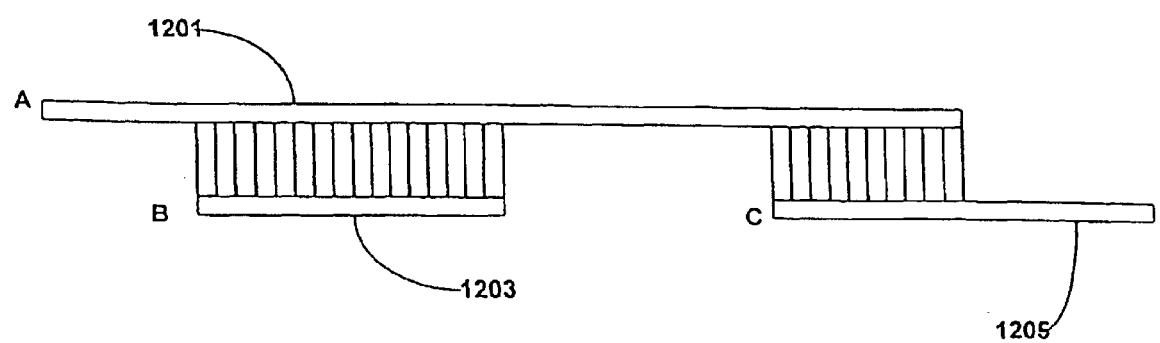
FIG._10

US 6,775,622 B1

METHOD AND SYSTEM FOR DETECTING NEAR IDENTITIES IN LARGE DNA DATABASES

CROSS-REFERENCE TO RELATED APPLICATIONS

This application claims the benefit of U.S. Provisional application No. 60/179,309 (filed Jan. 31, 2000), the contents of which are incorporated by reference.

COPYRIGHT NOTICE

A portion of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to the field of computer systems. More particularly, the present invention relates to a method and system for evaluating and comparing biological sequences using various computer related methods and systems.

BACKGROUND OF THE INVENTION

Computer programs and systems are known for generating and maintaining large databases of biological sequences (e.g., deoxyribonucleic acid (DNA), ribonucleic acid (RNA), amino acid sequences) derived from living organisms. Similarly, computer programs and systems are known for manipulating these databases in various ways to search for genes that can be used for various human testing, drug target identification and therapeutics.

As an illustration, the human genome, the complete, single-copy set of genetic instructions for a human, is being sequenced by many groups using several techniques with different purposes in an ongoing process. The various groups, techniques and purposes result in some fragments of the human genome being represented more than once in the genomic DNA databases. The inflated human genomic DNA database causes two problems addressed here. First, the time required to search the database is directly related to the size of the database. By removing redundancy from the database, the time to perform a search is reduced allowing more searches and more sensitive searches. Second, as searches are performed, the DNA sequences are annotated with the results. These annotations can be valuable and must be applied to all identical sequences in the genomic DNA database. A confounding factor is the dynamic nature of the genomic DNA database, wherein daily new sequences are added, old sequences removed and sequences are modified. For example, assume a sequence named ABC is in the genomic database and is annotated as "XYZ." This database could be updated tomorrow and the sequence formerly named ABC could then be called DEF. It is desirable to be able to apply the annotation "XYZ" to the sequence DEF.

Remote homologue detection (that is, detection of similarities within some range of similarity, such as <30%, etc.) has been the focus of many sequence similarity identification programs such as the Basic Local Alignment Search Tool (BLAST), hidden Markov models, and others. The BLAST programs are widely used tools for searching protein and DNA databases for sequence similarities.

While remote homologue detection will remain a central problem in bioinformatics, a critical technical problem presently exists in the attempt to quickly identify regions of near identity in large sequence databases.

There is a need in the art for a method of efficiently detecting near identities in large DNA databases in such a way as to make feasible a system to keep up with the daily additions that are being made to publicly available sequence databases.

There is a further need for such a system in order to provide solution mechanisms for hitherto unsolved problems such as: 1) removing redundancy from genomic sequence databases, 2) mapping (assembled) expressed sequence tags (ESTs)/sequence tagged sites (STSs)/complementary DNA molecules (cDNAs) onto genomic sequence, 3) assembling ESTs into the cDNAs they were derived from, and 4) searching EST/cDNA databases for alternately spliced cDNAs and single nucleotide polymorphisms (SNPs). An EST is a transcript corresponding to an expressed gene, the defined transcript sequence "tag" being a marker for a gene, which is expressed in a cell, a tissue, or an extract, for example. A SNP is an alteration in a single nucleotide base within a DNA sequence, which differs between individuals.

SUMMARY OF THE INVENTION

The present invention provides a solution to the needs described above through a system and method for detecting near identities in large DNA databases. The system and method disclosed herein make use of an algorithm used to construct and maintain a unique nucleotide database wherein the unique database contains no two DNA sequences such that one is contained in the other. The system and method are applicable to problems such as an all against all comparison of all available genomic sequence data, clustering and assembling ESTs into the cDNAs that generated the ESTs, mapping assembled ESTs onto genomic sequence, mapping cDNAs onto genomic sequences and locating alternately spliced cDNAs.

A system and method are disclosed for finding near identities in a DNA sequence database wherein tag arrays are generated for each of a first and a second database of sequences, and wherein near identities of sequences in the two databases are identified using a comparison model.

A system and method are also disclosed for finding near identities when the first and second databases are both genomic DNA sequence databases; when the first database is a genomic DNA database and the second database is a cDNA sequence database; when the first and second databases are both cDNA databases.

Similarly, a computer program stored on a computer readable medium or carrier wave is disclosed having computer code mechanisms for finding near identities in a DNA sequence database wherein tag arrays are generated for each of a first and a second database of sequences, and wherein near identities of sequences in the two databases are identified using a comparison model.

Also disclosed is a computer program for finding near identities in a DNA sequence database, the computer program having code mechanisms for generating tag arrays for each of a first and a second database of sequences, and wherein near identities of sequences in the two databases are identified using a comparison model.

Still other embodiments of the present invention will become apparent to those skilled in the art from the following detailed description, wherein is shown and described only the embodiments of the invention by way of illustration of the best modes contemplated for carrying out the invention. As will be realized, the invention is capable of modification in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3 illustrates a block diagram of the process of the preferred embodiment for generating sorted tag arrays and using these for finding near identifies in the relevant sequences.

FIG. 4 illustrates a block diagram of the preferred embodiment of the process of generating tags and creating a sorted tag array.

FIG. 5 illustrates a block diagram of the preferred embodiment of the process of comparing the tag arrays of various sequences and calculating various tests in order to find near identities of sequences.

FIGS. 6a–e illustrates a representation of the "SWISS-PROT like format" used in the preferred embodiment.

FIG. 10 illustrates exemplary sequences with complete identity and with overlapping identity.

DETAILED DESCRIPTION OF THE INVENTION

The present invention provides a solution to the needs described above through a system and method for detecting near identities in large DNA databases. The system and method disclosed herein make use of an algorithm used to construct and maintain unique DNA databases wherein the unique database contains no two DNA sequences such that one is nearly identical to a region of the other. The system and method are applicable to problems such as an all against all comparison of all the DNA sequences in a large DNA database, clustering and assembling ESTs into the cDNAs that generated the ESTs, mapping ESTs and assembled ESTs onto a genomic sequence, mapping cDNAs onto genomic sequences, and locating alternately spliced cDNAs.

1. Introduction

A. Operating Environment

The environment in which the present invention is used encompasses the general bioinformatics field, which includes the use of general purpose computers as well as special purpose computers and generally available database management systems.

Figure 1:
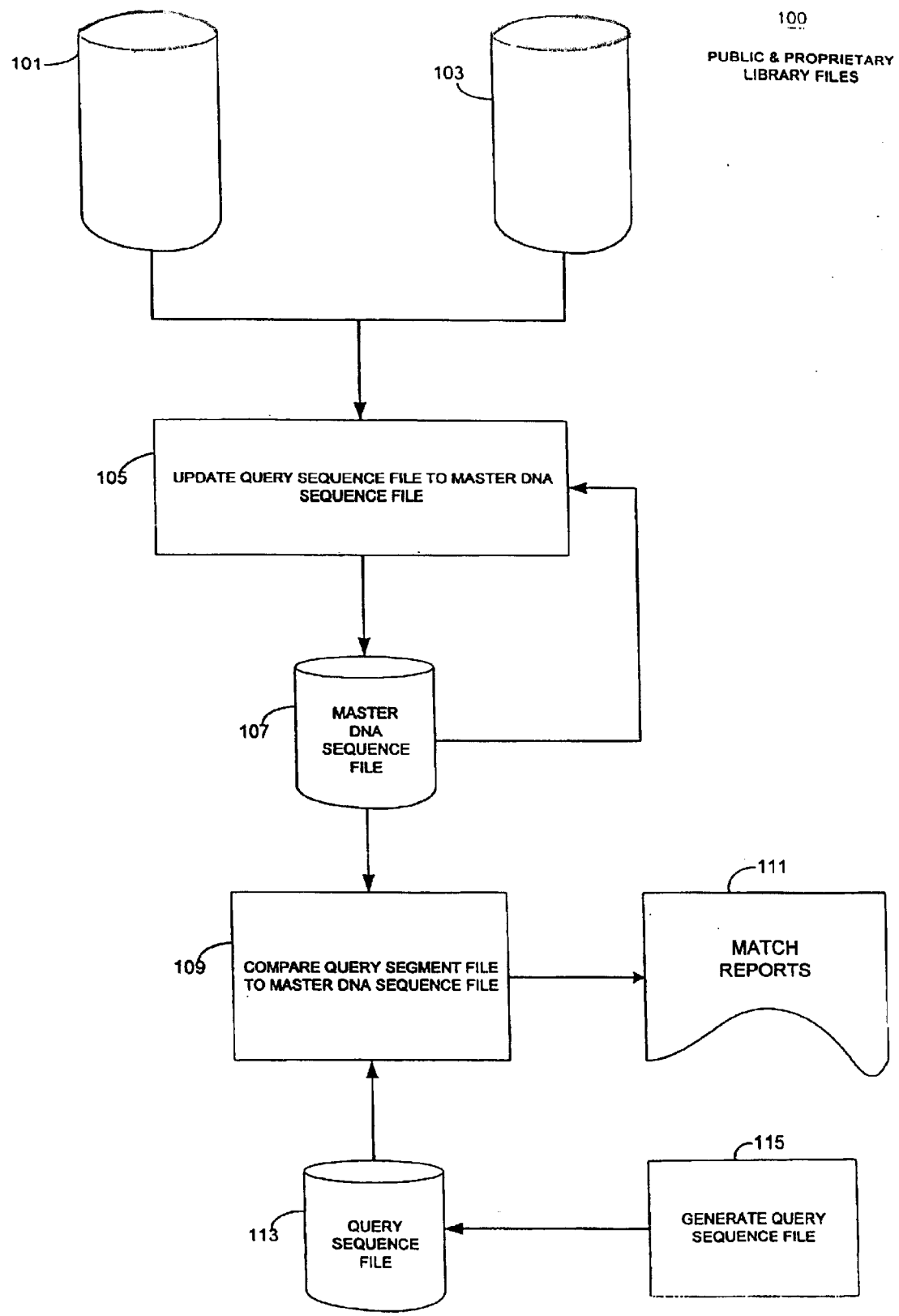
FIG. 1 illustrates a block diagram of the general process of using and updating a human genome sequence file.

The general field of bioinformatics and gene research using the human genome sequences defined to date can generally be described with reference to FIG. 1. Referring to FIG. 1 publicly available database files of the DNA sequences of the human genome 101, 103 are made available by a number of organizations such as the National Center for Biotechnology Information (NCBI; Bethesda, Md.), The Sanger Centre (Wellcome Trust Genome Campus, Hinxton, Cambridge UK), and Genome Sequencing Center (Washington University, St. Louis, Mo.). Such files, along with proprietary human genomic DNA databases, are typically used by research organizations to build and update 105 a master DNA sequence file 107. This master DNA sequence file 107 is then typically used together with some sort of query sequence file 113 wherein the sequences from the query file 113 are compared 109 with the master DNA file 107 to produce matching sequence reports 111 for use by researchers in further gene and related biomedical research. The query sequence files 113 may be generated 115 from other DNA sequence files, from cDNA data generated from cell samples using DNA sequencer programs, etc.

Figure 2:
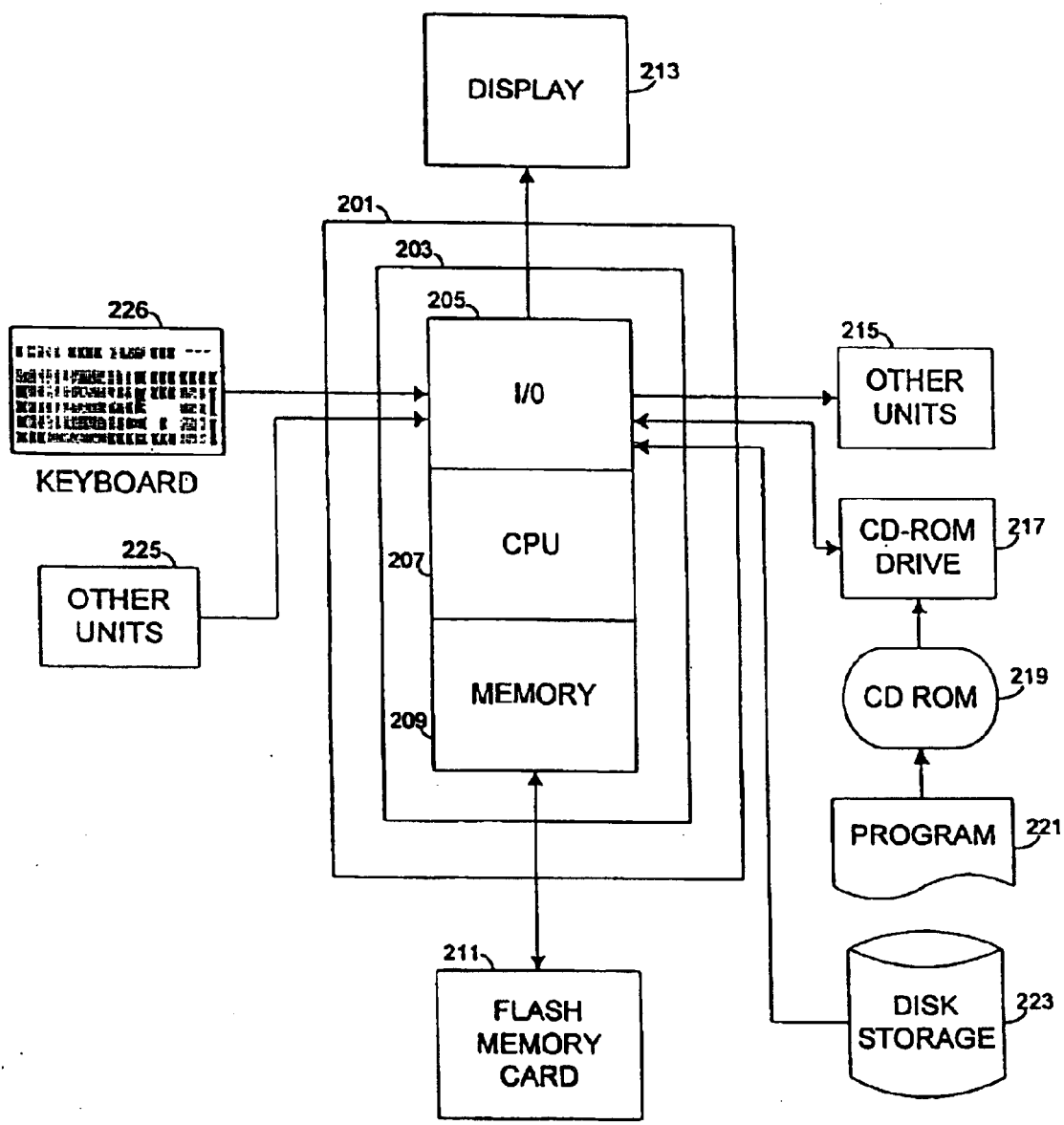
FIG. 2 illustrates a representative general purpose computer system configuration.

In the preferred embodiment a general purpose computer system is used. FIG. 2 illustrates an example of a computer system used to execute the software of the present invention. The general purpose system 201 includes a motherboard 203 having thereon an input/output ("I/O") section 205, one or more central processing units ("CPU") 207, and a memory section 209 which may have a flash memory card 211 related to it. The I/O section 205 is connected to a keyboard 226, other similar general purpose computer units 225, 215, a disk storage unit 223 and a CD-ROM drive unit 217. The CD-ROM drive unit 217 can read a CD-ROM medium 219, which typically contains programs 221 and other data. Logic circuits or other components of these programmed computers will perform series of specifically identified operations dictated by computer programs as described more fully below.

Unique Genomic Database

The algorithm presented here and the program developed from it can be used to construct and maintain a unique human genomic DNA database. The word "unique" is used to indicate that no two DNA sequences from the database exist such that one is nearly identical to a continuous portion of the other. While the techniques described in the preferred embodiment were developed to process human genomic DNA sequences, they are equally capable of processing DNA databases from other organisms. For example, the techniques described herein are currently being applied to genomic DNA databases generated from mouse, worm, and fish. Other genomic DNA databases are also being developed.

The algorithm and its implementation work with simple text strings. In the special case of DNA, the strings are over the alphabet A, C, G, and T. For example, the program reads and writes in the FastA format or the SWISS-PROT format, both of which are well known in the art. Examples of these formats may be found in various references, such as Bairoch, Amos, "Proteome Databases," in *Proteome Research: New Frontiers in Functional Genomics, Wilkins*, M. R. et al. (Eds.) pages 93–132, (Springer-Verlag 1997), Peruski, Jr., Leonard F., and Peruski, Anne H., *The Internet and the New Biology: Tools for Genomic and Molecular Research* (American Society for Microbiology 1997), and Ouellette, B. F. Francis, "The GenBank Sequence Database," in *Bioinformatics: A Practical Guide to the Analysis of Genes and Proteins, Baxevanis*, A. D. and Ouellette, B. F. F. (Eds.), pages 16–45 (Wiley-Liss, Inc. 1998). These references are incorporated fully herein by reference.

A sample of the SWISS-PROT format is shown in FIG. 6. The SWISS-PROT sequence format is a general purpose format used to store sequence data FIG. 6 illustrates one way of using the SWISS-PROT format with the ASIDE program.

The "ID" line 601 supplies the identifier "Z0" 603 and indicates that the DNA sequence is 753000 bases 605 in length. The second line, "AC," 607 gives the accession identifier for this sequence 609. In this example of ASIDE program implementation, the accession identifier 609 was the same as the "ID" identifier 603.

One or more "DR" lines 611, 613 follow in FIG. 6, in this case, 21 "DR" line entries. The purpose of a "DR" entry is to relate some external sequence (for example, a DNA sequence from GenBank) with the sequence given in the SWISS-PROT entry (Z0). Consider the second DR line 613 as an example. This line 613 indicates that the GenBank genomic DNA sequence "AQ474914" 617 that resides in the file "/vols/pdata/na/genomic/GEN_HUMAN.NDB" 619 is identical to Z0. The region of identity is position 1 to position 289 621 in AQ474914 with position 557888 to 558176 623 in Z0. These numbers may be negative to indicate that the match is in the reverse orientation. The length of AQ474194 is given as 350 bases 625 and the length of Z0 is given as 753000 bases 627. In this case, the match between Z0 and AQ474194 is composed of nine 629 32 base pair matches. The position on the DR line with a value of −1.00 631 is used to store the Spearman correlation coefficient when it is computed. In this example, the Spearman correlation coefficient is not computed. The value 0.00 633 is the median difference indicating that there are no gaps in the alignment between Z0 and AQ474194. Finally, the value 262 635 is, when interpreted as a binary number, a set of flags indicating various features about the alignment between Z0 and AQ474194. The binary representation of 262 is 0000000100000110. Let the rightmost digit be number 1 and the leftmost digit be number 16. The meaning of each digit is given in the table below.

1 The number of hits is more than the minimum (5 by default)
2 The median difference is less than the maximum (25 by default)
3 The hit density is greater than the minimum (0.25 by default)
4 not used
5 not used
6 not used
7 not used
8 Match was in opposite orientation
9 The database sequence is contained in the query sequence
10 The 3' end of the database sequence is contained in the 5' end of the query sequence
11 The 5' end of the database sequence is contained in the 3' end of the query sequence
12 One sequence is completely contained in the other
13 not used
14 not used
15 not used
16 not used The value of 262 635 of the example DR line 613 indicates that the median difference is less than the maximum, the hit density is greater than the minimum, and the database sequence is contained in the query sequence. The last element of the DR line 636 is the result of the time function in the programming language C. This is typically the number of seconds since Jan. 1, 1970. The SQ line 637 indicates the length the sequence and the DNA sequence 639 immediately follows.

In the preferred embodiment, a system and method for using the invention makes use of a program called "ASIDE" ("A Sequence IDentity Enumerator") for clustering sequences according to the invention. The clustering is useful, because it reduces the redundancy in the sequences to be analyzed, and it allows the annotations on one sequence to be automatically applied to other sequences that are identical to it In the example detailed herein, the source of the genomic data that is being clustered is primarily from the GenBank database at the NCBI, and the Sanger Centre. GenBank is part of the International Nucleotide Sequence Database Collaboration, which is comprised of the DNA DataBank of Japan (DDBJ), the European Molecular Biology Laboratory (EMBL), and GenBank at NCBI. These three organizations exchange data on a daily basis. The Sanger Centre is a genome research centre founded by the Wellcome Trust and the Medical Research Council.

While these databases are used in the preferred embodiment, those skilled in the art will recognize that other databases of biological sequence data (DNA, RNA, protein, etc.) with different formats can be readily used as well. Accordingly, while the present invention can be used with any DNA database, the human genome sequence described below is but one example of such use.

2. Algorithm for Identifying Near Identities Between and Within Databases of DNA Sequences A technical problem confronting all bioscience researchers in this field is the huge size of the DNA databases. It is not unusual for the master DNA file to have millions of records (sequences) composed of billions of bases. The computer time required to compare these sequences grows as the size of the files grow, even when using reasonably fast computer processors.

An algorithm has been developed and implemented that is capable of very quickly identifying near identities between and within databases of DNA sequences. As an example of the utility of this algorithm, all identical regions between pairs of ESTs from the public EST database can be found in about 8 hours. Previously, this type of comparison would have taken at least four months, on the same computer.

The idea of "near identity" is based on the observation that the DNA sequence which is generated by a sequencing process from some source DNA will contain errors. Some sequencing processes are more prone to errors than others. Two sequences are "nearly identical" if the differences between the two can be reasonably explained by the error rate of the sequence generation process. For example, when comparing two ESTs, about 2 differences per 100 nucleotides are expected so it might be reasonably considered that ESTs with fewer than 5% differences are "nearly identical." Another example is a finished genomic DNA sequence where the error rate is expected to be well below 1 per 1000 bases. When comparing finished genomic DNA sequences, one might require fewer than 1% difference between two sequences before they are characterized as nearly identical. In the methods discussed herein relative to the preferred embodiment, the definition of "nearly identical" can easily be appropriately defined for the pairs of DNA sequences being compared.

The present invention provides a system and computer implemented method for finding near identities within and between large DNA databases. The method used to enumerate regions of near identity is composed of two phases; the tag list construction phase and the sequence searching phase.

Figure 7:
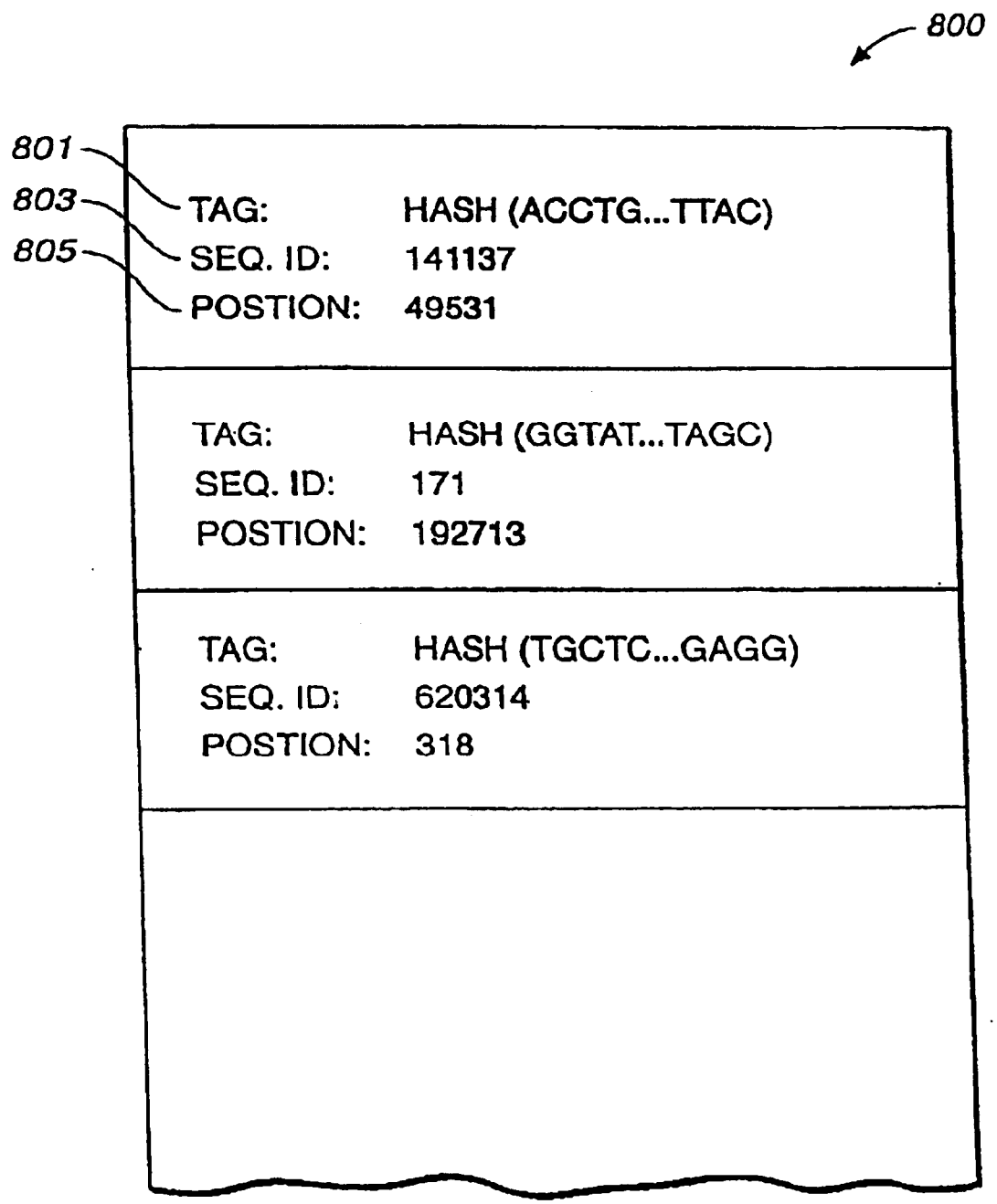
FIG. 7 illustrates an exemplary format of a data structure used as a sorted tag array in the preferred embodiment.

A tag is a representation of a small segment of a DNA sequence. These tags are used to build a compact data structure, the tag array, which can be searched quickly. FIG. 7 depicts an exemplary tag data structure record as used in the preferred embodiment. In FIG. 7 the representative record includes a tag value 801, a sequence ID 803 and a tag position value 805 which represents the location (position) in the sequence of this tag. A "Sequence ID" 803 is a unique identifier, typically an integer, assigned to a DNA sequence when it is first read from the database. All subsequent references to the sequence will use the assigned sequence ID. For example, in the preferred embodiment, the ASIDE system assigned the sequence ID "1" to the first DNA sequence read, "2" to the second sequence and so on until all sequences have been read and recorded. The term "Position" as in "tag position value 805" is defined as follows: position "I" of the DNA sequence "S" refers to the subsequence starting with the ith nucleotide. For example, the sequence "ATTG" appears at position 4 in the sequence "GCAAT-TGCTT" (SEQ ID NO:4). Phase I scans the DNA sequences in the database file and selects sufficient tags from each sequence to ensure that regions of near identity between a DNA sequence from the database file and a DNA query sequence will be recognized. Sufficiency depends on the sequences being compared, and the error rate expected in the sequences. Long sequences or highly accurate sequences require a low density of tags to ensure that they are recognized as "nearly identical" to other long or highly accurate sequences. Short or highly inaccurate sequences require a high density of tags to ensure that they are recognized as "nearly identical" to other short or highly inaccurate sequences. For example, in the preferred embodiment, in using the ASIDE system to cluster genomic sequences (long and moderately accurate) one key every 32 nucleotides is generated, whereas in using the ASIDE system to cluster ESTs (short and highly inaccurate) one key every 16 nucleotides is generated. Phase II compares each DNA sequence from the query set with the tag array to identify all DNA sequences from the database file that contain a region of near identity to the DNA query sequence.

A "tag" is an integer representation of a short DNA fragment, typically 32 nucleotides in length. The DNA fragment can easily be represented as the integer $$L = \sum_{i=1}^{|DNA|} I(DNA_i) \cdot 4^{(i-1)}$$

where L is an integer representation of $DNA_1$, $DNA_2$, ... $DNA_{32}$, $DNA_i$ is the ith base in the DNA fragment, $|DNA|$ is the length of the DNA fragment, typically 32 in the preferred embodiment, and where $I(DNA_i)$ evaluates to 0, 1, 2, and 3 when $DNA_i$ is A, C, G, and T respectively.

In practice, it is difficult to work with this representation of DNA fragments due to the magnitude of the integer L that results for all but the smallest DNA fragment There are several methods that can be used to decrease the size of the integer L. A subset of the nucleotides in the DNA fragment could be used. For example, "consider only the nucleotides 1, 3, 5, ..." Or possibly, "consider only the leftmost 'x' and rightmost 'y' nucleotides." Another method would be a hashing method using the "multiplication method" as discussed by Thomas E. Corman, Charles E. Leiserson, and Ronald L. Rivest, Introduction to Algorithms (MIT Press 1990). In this method, the hash value of L, called "h(L)", is computed as $$h(L) = \left\lfloor 2^{16} \left( L \frac{\sqrt{5}-1}{2} MOD\ 1 \right) \right\rfloor$$

This results in a value of "h(L)" between 0 and $2^{16}$ for any value of L.

The preferred method is generally referred to as "the division method." This method is preferred because it can be modified as in the function NEXT-TAG to compute the hash very quickly.

An exemplary method of generating tags and sequence ID tag positions is shown in FIG. 4. Those skilled in these arts will recognize that other similar methods may be used to accomplish a similar purpose.

To facilitate the practical use of the representation shown above for L, a tag is defined as L modulo P where P is a large prime number such that P·4 can be stored in one computer word. For example, in the preferred embodiment P=1073741783. The tag, T, for a DNA fragment may be computed as $$L = \sum_{i=1}^{|DNA|} I(DNA_i) \cdot 4^{(i-1)} \bmod P$$

When the length of the DNA sequence fragment exceeds half the number of bits in a computer word, some tags will represent more than one DNA sequence fragment. While identical tags do not guarantee identical sequences, identical sequences do guarantee identical tags and can be used to narrow the set of sequence pairs that contain nearly identical DNA sequence. In a preferred embodiment tags are computed with the functions shown in Tables 1 and 2 below. Many of the modulo operations are not required since the result will not be larger than P and so are eliminated in Table 1. For example, when length=32 and P=1073741783 (as in the preferred embodiment), the time required to compute a tag is ½ of the time required by an alternative method (sometimes called the Nieve method). This alternative method would have lines 2, 3, 4 and 5 removed from Table 1 below.

When computing tags for the DNA fragments $s_i s_{i+1}$ ... $s_{i+31}$, $s_{i+1} s_i s_{i+2}$ ... $s_{i+32}$, ... from the string S, knowing the previous tag can greatly decrease the time needed to compute the current tag. For example, for DNA sequence

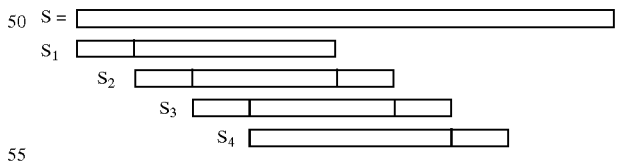

tags for the subsequences $S_1$, $S_2$, $S_3$, $S_4$ etc. must be calculated.

If the tag "$T_1$" for $S_1$ is known, then almost all of the computation is already done for the computation to find tag "$T_2$" for $S_2$. The only differences between $S_1$ and $S_2$ are the first nucleotide of $S_1$ and the last nucleotide of $S_2$. To compute $T_2$ from T one need to remove the value that the first nucleotide of $S_1$ contributed to T, and add the value that the last nucleotide of $S_2$ would contribute to T. In the preferred embodiment, when length=32 and P=1073741783, the function in Table 2 below is approximately sixteen times faster than the Nieve method and eight times faster than the function Table 1.

Table 2 subtracts from the previous tag, the value contributed by the most significant nucleotide of the previous fragment and adds the value of the least significant nucleotide of the current fragment.

TABLE 1

Function for Generating Tags

```
function GENERATETAG (DNA, length)
1    T = 0; i = 0
2    while ((T < P) and (i < length))
3        T = T · 4 + I(DNA_i)
4        i = i + 1
5    T = T mod P
6    while (i < length)
7        T = T · 4 + I(DNA_i) mod P
8        i = i + 1
9    return (T)
```

Here "DNA" is a given sequence and "length" is 32 and T is the tag value 801 in FIG. 7. For example GENERATETAG (DNA, 32). The function GENERATETAG computes a tag value for the given DNA sequence and length=32. For example, if DNA=actgagctactctgccactcttctactggacc (SEQ ID NO:1), for length=32 and P=1073731783, the tag will equal 788943246. Initially, the value of T will be smaller than P so there is no need to perform the modulo operation. In practice, this eliminates approximately one half of the modulo operations.

TABLE 2

Improved Function for Generating Tags.

```
function NEXTTAG (DNA, length, T_p, pb)
1    T = (T_p − (I(pb) · 4^(length−1))) mod P
2    T = (T · 4 + I(DNA_(length−1))) mod P
3    return (T)
```

If we let $T_p$ be the tag for $s_i s_{i+1} \ldots s_{i+l-1}$ for i>0, we can compute T for $s_{i+1} s_{i+2} \ldots s_{i+l}$ using two modulo operations. The parameter pb is the nucleotide immediately preceding the DNA fragment for which we are computing the tag. In line 1 in a preferred embodiment, the powers of 4 modulo P have been precomputed. For example, an exemplary output of the preferred embodiment which demonstrates the functions shown in Tables 1 and 2 with the exemplary nucleotide sequence "CTGAGCTACTCTGCCACTCTTCTACTG-GACCTG" (SEQ ID NO:2).

Illustrative Results of Running test_gen_key.
generate_key called

```
DNA       ctgagctactctgccactcttctactggacct
length    32
Prime     1073741783
First loop (no modulo operations)
DNA [1] = c      1
DNA [2] = t      7
DNA [3] = g      30
DNA [4] = a      120
DNA [5] = g      482
DNA [6] = c      1929
DNA [7] = t      7719
DNA [8] = a      30876
```

-continued

```
DNA [9] = c      123505
DNA [10] = t     494023
DNA [11] = c     1976093
DNA [12] = t     7904375
DNA [13] = g     31617502
DNA [14] = c     126470009
DNA [15] = c     505880037
Second loop (with modulo operations)
DNA [16] = a     949778365
DNA [17] = c     577888112
DNA [18] = t     164068885
DNA [19] = c     656275541
DNA [20] = t     477618601
DNA [21] = t     836732624
DNA [22] = c     125705148
DNA [23] = t     502820595
DNA [24] = a     937540597
DNA [25] = c     528937040
DNA [26] = t     1042006380
DNA [27] = g     946800173
DNA [28] = g     565975345
DNA [29] = a     116417814
DNA [30] = c     465671257
DNA [31] = c     788943246
DNA [32] = t     1008289421
Returning 1008289421
next_key called
    DNA     tgagctactctgccactcttctactggacctg
    length  32
    key     1008289421
    Prime   1073741783
```

Remove value of the previous base (c)

updated key 1008282697

Add value of last base (g)

Returning 811905441

In the preferred embodiment, these results are produced from an exemplary coding of the two functions shown above, which coding is now illustrated with the sequence "CTGAGCTACTCTGCCACTCTTCTACTG-GACCTGGTCAACTAGCCAGCATG" (SEQ ID NO:3). Those skilled in these arts will understand that the two functions described above may be coded in many ways to produce the desired results.

test_gen_key.c

```c
#include <stdio.h>
#include "bdb.h"
#include <math.h>
main ( )
{
  char *str, *inv_comp_str;
  unsigned int four_pow [32];
  int i, next, key, info_counts [4];
  double jh_log [32];
  extern int generate_key ( );
  extern int next_key ( );
  extern double info2 ( );
  extern double next_info ( );
  /*
   * Compute the logs that are needed for info computations.
   */
  for (i=0; i<32; i++) {
    jh_log [i]=log (((double)(i+1))/((double)32))/
       LOG2;
  }
  /*
```

```
 * Compute powers of four mod BIG_PRIME.
 */
four_pow [0]=1;
for (i=1; i<32; i++) {
  four_pow [i]=(four_pow [i-1]* 4) % BIG_PRIME;
}
str =
  "ctgagctactctgccactcttctactg-
  gacctggtcaactagccagcatg";
key=generate_key (str, 32);
next=next_key (str+1, 32, key, four_pow);
/* info2 (str, 32, info_counts, jh_log); */
/* next_info (str+1, 32, info_counts, jh_jog); */
}
``` example-generate-keys.c

```
/*
 * This function computes a hash value for the string str. The
 * hash value is the base 4 representation of the string modulo
 * BIG_PRIME. This function spends a lot of time computing
 * the "%" function and can be sped up when repeated called on
 * successive windows of a large string by updating the previous
 * key value. See the function "next_key".
 *
 * Copyright (c) 1999 Jim Holloway, ZymoGenetics Inc.
 * $Id: generate_key.c,v 1.1 1999/05/10 16:06:21 holloway Exp $";
 * $Log: generate_key.c,v $
 * Revision 1.1 1999/05/10 16:06:21 holloway
 * Initial revision
 *
 */
static char rcsid [ ]="$Id: generate_key.c,v 1.1 1999/05/
  10 16:06:21 holloway Exp $";
#include "bdb.h"
unsigned int generate_key (str, len)
  char *str;
  int len;
{
int i, limit;
unsigned int ret_val=0;
fprintf (stdout, "generate_key called\n\n");
fprintf (stdout, "\tDNA\t%.32s\n", str);
fprintf (stdout, "\tlength\t%d\n", len);
fprintf (stdout, "\tPrime\t%d\n\n", BIG_PRIME);
limit=MIN (len, LOG_BIG_PRIME);
fprintf (stdout, "First loop (no modulo operations) \n\n");
for (i=0; i<limit; i++) {
  fprintf (stdout, "DNA [%d]=%c\t", i+1, str [i]);
  switch (str [i]) {
  case 'c': ret_val=(ret_val * 4+1);
    fprintf (stdout, "%d\n", ret_val);
    break;
  case 'g' ret_val=(ret_val * 4+2);
    fprintf (stdout, "%d\n", ret_val);
    break;
  case 't' ret_val=(ret_val * 4+3);
    fprintf (stdout, "%d\n", ret_val);
    break;
  default: ret_val=(ret_val * 4);
    fprintf (stdout, "%d\n", ret_val);
    break;
  }
}
fprintf (stdout, "\nSecond loop (with modulo operations) \n\n"
for (i=limit; i<len; i++) {
  fprintf (stdout, "DNA [%d]=%c\t", i+1, str [i]);
  switch (str [i]) {
  case 'c': ret_val=(ret_val * 4+1) % BIG_PRIME;
    fprintf (stdout, "%d\n", ret_val);
    break;
  case 'g' ret_val=(ret_val * 4+2) % BIG_PRIME;
    fprintf (stdout, "%d\n", ret_val);
    break;
  case 't' ret_val=(ret_val * 4+3) % BIG_PRIME;
    fprintf (stdout, "%d\n", ret_val);
    break;
  default ret_val=(ret_val * 4) % BIG_PRIME;
    fprintf (stdout, "%d\n", ret_val);
    break;
  }
}
fprintf (stdout, "\nReturning %d\n\n", ret_val);
return (ret_val);
}
``` example_next_key.c

```
/*
 * This function, given the hash value for the previous window
 * (offset -1) returns the hash value for the current window
 * pointed to by str. The hash value is the base 4 representation
 * of the string modulo BIG_PRIME. The function "generate_key"
 * will compute this function without need of the previous value.
 *
 * Copyright (c) 1999 Jim Holloway, ZymoGenetics Inc.
 *
 * $Id: next_key.c,v 1.1 1999/051/10 16:06:21 holloway Exp $
 *
 * $Log: next_key.c,v $
 * Revision 1.1 1999/05/10 16:06:21 holloway
 * Initial revision
 *
 */
static char rcsid [ ]"$Id: next_key.c,v 1.1 1999/05/10
  16:06:21 holloway Exp $;
#include "bdb.h"
unsigned int next_key (str, len, prev_key, four_pow)
  char *str;
  int len;
```

```
unsigned int prev_key, *four_pow;
{
unsigned int change=0, prev_change=0;
fprintf (stdout, "next_key called\n\n");
fprintf (stdout, "\tDNA\t%.32s\n", str);
fprintf (stdout, "\tlength\t%d\n", len);
fprintf (stdout, "\tkey\t%d\n", prev_key);
fprintf (stdout, "\tPrime\t%d\n\n", BIG_PRIME);
/*
 * Remove the leading character
 */
fprintf (stdout, "Remove value of the previous base (%c)
    \n", str [-1]);
switch (sir [-1]) {
/*case 'a': change=0 * four_pow [len-1]; break; */
case 'c': change=four_pow [len-1]; break;
case 'g': change=2 * four_pow [len-1]; break;
case 't': change=3 * four_pow [len-1]; break;
}
/*
 * Subtract change mod BIG_PRIME
 */
prev_change=change;
while ((change>prev_key) && (prev_change>=
    change)) {
prev_change=change;
change -=BIG_PRIME;
}
prev_key -=change;
while (prev_key>BIG_PRIME) {
  prev_key -=BIG-PRIME;
  }
fprintf (stdout, "updated key\t%d\n\n", prev_key);
/*
 * Add the last character
 */
fprintf (stdout, "Add value of last base (%c) \n", str [len
    -1]);
switch (str [len -1]) {
case 'c': prev_key=(prev_key * 4+1) % BIG_
    PRIME; break;
case 'g': prev_key=(prev_key * 4+2) % BIG_
    PRIME; break;
case 't': prev_key=(prev_key * 4+3) % BIG_
    PRIME; break;
default: prev_key=(prev_key * 4) % BIG_PRIME;
    break;
}
fprintf (stdout, "Returning %d\n\n", prev_key);
return (prev_key);
}
```

Some regions of DNA sequences are repeated throughout the genome and are of little value in identifying a sequence generated from the same region of the genome. To decrease the number of false positive identities reported, regions of the query DNA sequences with low information content are not used to search the sorted tag array. Further, micro-satellites are identified and not used to search the sorted tag array. These concepts of false positives, low information content and micro-satellites are now described.

In a preferred embodiment, a "false positive" identity is defined as the situation which occurs when the program claims two DNA sequences share an identical region, when in fact, distinct pieces of DNA generated the sequences. For example, the DNA fragment "AAA . . . AA" appears many times in the human (and others) genome. Claiming that all DNA sequences that contained "AAA . . . AA" were generated from the same piece of DNA is a false positive. Similarly, a "false negative" occurs when, in fact, two DNA sequences were generated by the same piece of DNA, but the program fails to claim that they are nearly identical.

A measure of "information" contained in a DNA sequence can be estimated by counting the number of yes/no questions required to determine the next nucleotide in the DNA sequence. For example, if the DNA sequence is "AAA . . . AA" one can, with high confidence, predict that the next nucleotide in the sequence is A without asking any additional questions. On the other hand, if the randomly generated DNA sequence is "CTCGAAAT . . . GGTC" (SEQ ID NO:5) one needs to ask two questions to be confident of predicting what the next nucleotide is. One would ask "Is the next nucleotide A or T?" If yes, the second question is "is the next nucleotide an A?" On the other hand, if the answer is no, then the second question is "is the next nucleotide a C?" From the answers the next nucleotide can be predicted. In the first example, the next nucleotide could be predicted with zero questions asked, so the information content of the DNA sequence is "zero" questions (or bits) per nucleotide. In the second example, two questions were required, indicating that the information content is two questions (or bits) per nucleotide. With this concept a function can be defined to measure the information content of DNA sequences that returns a real number between 0 and 2. This function is shown below in Table 3.

TABLE 3

Information Content of DNA Sequence.

```
function INFO4 (DNA, length)
1    i = 0 C[0]=C[1]=C[2]=C[3]=0
2    while (i < length)
3        C[I(DNA_i)] = C[I(DNA_i)] + 1
4        i = i + 1
5    i = 0 S = 0
6    while (i < 4)
7        if (C[I(DNA_i)] > 0)
8            S = S + (C[I(DNA_i)] * log_2(C[I(DNA_i)] - 1)
9        i = i + 1
10   S = S/length
11   return (-S)
```

Lines 2, 3 and 4 of this function compute the distribution of nucleotides in the DNA sequence supplied. Lines 5–9 compute a measure of information contained in the DNA sequence. Lines 10–11 normalize the information to "information per nucleotide." An example computation is as follows:

```
Info4 called
    DNA       ctgagctactctgccactcttctactggacct
    length    32
    Nucleotide distribution
        A     5
        C     12
        G     5
        T     10
    Information = 1.892
```

Referring once again to the following diagram

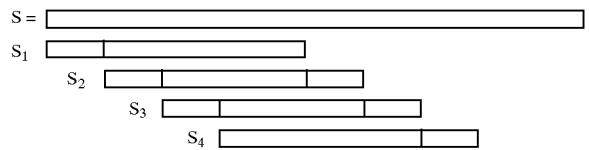

For a given DNA sequence S, information measures must be calculated for the many windows of S. Again, it is noted that once the information value is computed for $S_1$, much of the work needed to compute the information value for $S_2$ has already been done. For example, let $S_1$="CT ... G" and let the distribution of nucleotides (computed by lines 2–4 in function INFO4) be A=7, C=8, G=12 and T=5. Now if $S_2$="TA ... GA" the distribution of nucleotides for $S_2$ can be calculated as follows

|     | $S_1$ | Δ  | $S_2$ |
| --- | ----- | -- | ----- |
| A = | 7     | +1 | 8     |
| C = | 8     | -1 | 7     |
| G = | 12    |    | 12    |
| T = | 5     |    | 5     |

The only change between the distribution of nucleotides in $S_1$ and $S_2$ is the first nucleotide in $S_1$ (a C) and the last nucleotide in $S_2$ (an A). To compute the distribution of $S_2$, subtract 1 from the number of Cs in the $S_1$ distribution and add 1 to the number of As in the $S_1$ distribution. The function NEXTINFO4 in Table 4 implements this idea in lines 1 and 2. Lines 3–9 in Table 4 are the same as lines 5–11 in Table 3.

TABLE 4

Improved Method to Assess Information Content of DNA Sequence

```
function NEXTINFO4 (DNA, length, Cp, pb)
1    C[I(pb)] = C[I(pb)] - 1
2    C[I(DNA_{length-1})] = C[I(DNA_{length-1})] + 1
3    i=0 S=0
4    while (i < 4)
5        if (C[I(DNA_i)] > 0)
6            S = S + (C[I(DNA_i)] * log_2(C[I(DNA_i)] - 1)
7        i = i + 1
8    S = S/length
9    return (-S)
```

For example;

```
NextInfo4 called
    DNA      tgagctactctgccactcttctactggacctg
    length   32
Subtracted one from the count of C
Added one to the count of G
Nucleotide distribution
    A    5
    C    11
    G    6
    T    10
    Information = 1.925
```

Low information regions of DNA occur frequently in genomic DNA and lead to false positives. By measuring the information content of each region of DNA, such regions of low information can be avoided in determining regions of near identity.

"Microsatellites" are regions of DNA sequences that have multiple repeats of a short DNA sequence. For example, the sequence " ... ATCATCATCATCATC ... " (SEQ ID NO:6) and " ... GAGAGAGAGAGA ... " (SEQ ID NO:7) are microsatellites. These sequences occur more frequently than expected in a random DNA sequence and can lead to false positives. The single base repeats (" ... AAAAA ... ") and dinucleotide repeats (" ... GAGAGA ... ") will be recognized by the function INFO4. However, the function INFO4 will not recognize the microsatellite " ... AGCTAGCTAGCTAGCTAGCT ... " (SEQ ID NO:8) since the distribution of nucleotides is even (i.e., A=5, G=5, C=5, and T=5). To recognize this and other Microsatellites one notes that A is always followed by G, G is always followed by C, C is always followed by T and T is always followed by A.

The distribution of nucleotide pairs (dinucleotides) is

|   | A | G | C | T |
|---|---|---|---|---|
| A | 0 | 5 | 0 | 0 |
| G | 0 | 0 | 5 | 0 |
| C | 0 | 0 | 0 | 5 |
| T | 5 | 0 | 0 | 0 |

In the preferred embodiment, the functions INFO16 and NEXINFO16 compute the information content of DNA sequences based on the distribution of dinucleotides in the DNA sequence. These functions in the preferred embodiment take more compute time to evaluate than the functions INFO4 and NEXTINFO4 since there are 16 classes to examine rather than 4.

The genomic DNA of organisms contain "repetitive elements." A repetitive element is a region of DNA that is a few hundred nucleotides in length that appears frequently in the organisms DNA. These regions of highly similar DNA, although from different parts of the genome, can lead to false positive near identity predictions. Databases exist which contain known repetitive elements. The process described here to recognize near identities can be used to recognize and remove repetitive elements from a genomic sequence. Once the repetitive elements have been removed, the genomic sequences can be compared to one another without risk of a false positive due to a repetitive element.

3. Searching for Nearly Identical Regions

In a preferred embodiment, tags of length l are generated every n nucleotides for each DNA sequence in the database. In the exemplary applications discussed below, l=32 and n=32. The tags 801 in FIG. 7 along with the sequence ID 803 and position the tag was generated from 805, are sorted numerically by the tag value 801 and stored in the sorted tag array 800. The sorted tag array 800 can be searched for a particular tag quickly using the standard binary search algorithm described by Donald E. Knuth. *The Art of Computer Programming, Volume 3, Sorting and Searching*, Second Edition (Addison-Wesley, 1998).

This general process is explained now with reference to FIG. 3. The process begins by reading a DNA sequence file (here called the D file) and generating tags as described above and writing them to a tag array as defined in FIG. 7 (here called the "Dtag" array) 303. The Dtag array is then sorted on tag value 305. Then a query DNA sequence file (Q) is read and tags (here Qtags) are generated 307 and the Qtag array sorted as before. Then each Qtag is read and used to search the Dtag array for any matches 309. Matches are recorded and used in various ways (as explained more fully below) to find identical regions in Q and D 311.

This process is described more fully in FIG. 5. More specifically, in a preferred embodiment, once the sorted tag array has been built 503, 505, each of the query DNA sequences is considered. For the query DNA sequence Q, the tags for each of the length l subsequences $q_i q_{i+1} \ldots q_{i+l-1}$ are used to search the sorted tag array 511. Each search will locate all tags from the DNA sequence database (db) that are identical to the tag for $q_i q_{i+1} \ldots q_{i+l-1}$. For every tag from the db that is identical to a tag from Q, a match is noted that records the position of the db tag and the position of the query tag 513.

Consider the m matches between the db sequence D and Q. These matches are used to identify regions of near identity between D and Q. In addition to regions of near identity, one must also consider both DNA fragment duplication in unrelated DNA sequences and distinct DNA fragments generating identical tags. In a preferred embodiment, three methods are used to identify regions of identity: (1) the absolute number of tags in common between D and Q, (2) the density of common tags relative to the maximum density of common tags, and (3) the relative ordering of the tags on D and Q.

If Q and D are identical DNA sequences, each of the $[|D|/n]$ tags generated from D will match a tag from Q. Here "$|D|$" is the number of nucleotides in a sequence and "$[|D|/n]$" is the maximum number of tags found, where "n" is the number of nucleotides between tags. As Q and D diverge from one another, we expect the number of matching tags to decrease. Match density is the ratio of observed matching tags to $[|D|/n]$. That is, if D had a total of 120 tags originally, and the number of matching tags between Q and D was 60, the match density is 60/120 or 0.5. The match density may be used to identify nearly identical DNA sequences. The match density required is dependent on the same features that define "near identity," i.e., sequencing error rate and sequence length. Based on empirical studies, in the preferred embodiment a match density of 0.25 is the minimum value between two sequences used to call them "nearly identical." However, for very short sequences, such as ESTs, a larger value, such as 0.5 is used since the absolute number of matches between short sequences is small. Similarly, the match density may be computed for a subsequence of D allowing us to identify regions of near identity within larger DNA sequences 521, 523.

FIG. 5 is an exemplary method of matching D tags to Q tags. Those skilled in these arts will recognize that various similar methods for making such matches may be used.

The order of the tags in D can be compared with the order of the tags in Q and used to recognize nearly identical DNA sequences. For example, if Q and D contain a region of identity, the difference between the tag position in Q and the corresponding tag position in D should be equal for all matches. A measure can be constructed by finding the median difference m and the corresponding tag positions and then computing the sum of the differences between the median and each of the differences. Dividing this sum by n gives the "average deviation from the median difference." This "average deviation from the median difference" can be used to identify regions of Q and D that contain a nearly identical region 525.

Figure 8A:
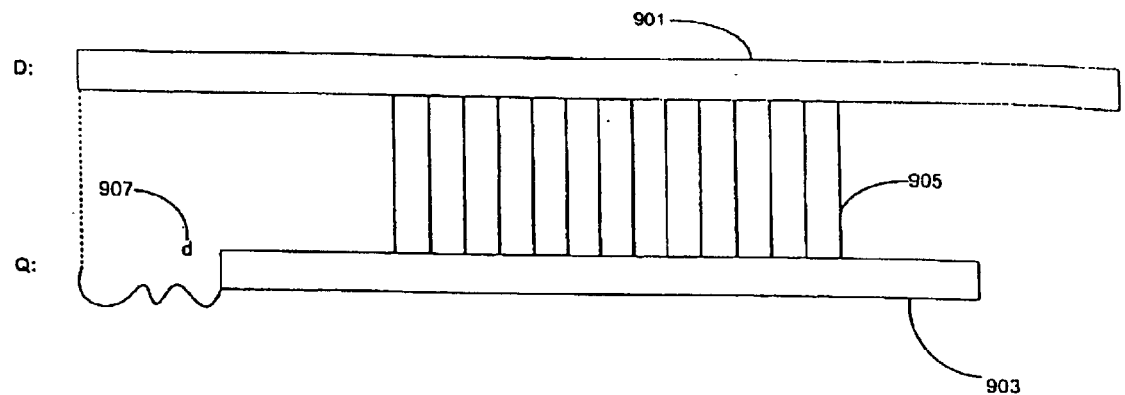
FIGS. 8A and 8B illustrate two exemplary types of identities between two DNA sequences.
Figure 8B:
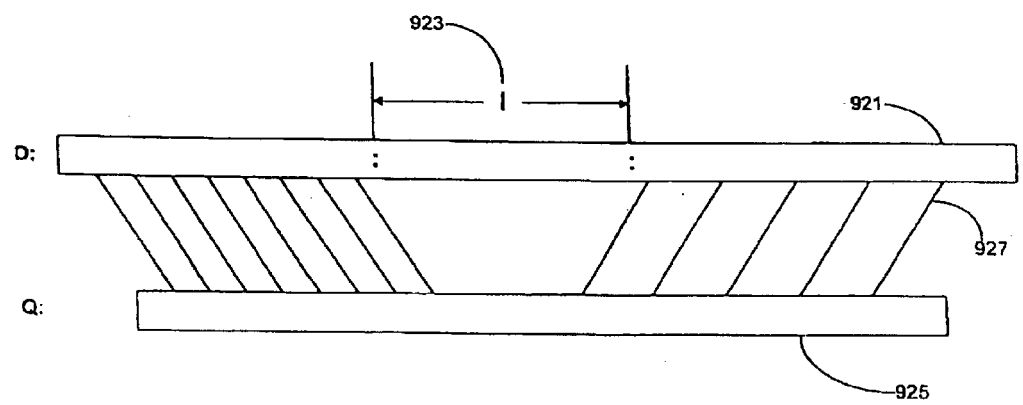

For example, referring to FIGS. 8A and 8B the lines 905 between sequence D 901 and sequence Q 903 and lines 927 between sequence D 921 and sequence Q 925 indicate regions of identity. FIG. 8A illustrates a perfect match between Q 903 and a region of D 901. On the other hand, FIG. 8B shows a match between Q 925 and D 921 where a region I 923 has been inserted into D 921 relative to Q 925. In the sequencing process, the sequencing systems will occasionally insert one or a few nucleotides into a sequence and the preferred embodiment of the invention is capable of accommodating these errors. The number and size of the inserts are dependent on the quality of the sequencing process or system used. It is desirable to be able to distinguish between poor sequencing of the same region of DNA and between two distinct but similar regions of DNA.

Referring again to FIG. 8A assume that the first nucleotide in Q 903 matches the 11th nucleotide in sequence D 901. Thus, there is a difference of 10 nucleotides between a nucleotide in Q 903 and the corresponding nucleotide in sequence D 901. Since it is a perfect match, it is clear that there is always a difference of 10 between corresponding nucleotides. One can list all of the differences (i.e., 10, 10, 10, 10, etc.) and calculate the median (which here is 10). To measure the quality of the match one can evaluate how different the median is from each of the differences.

For the match depicted in FIG. 8A that would be $$\frac{(10-10) + (10-10) + \ldots + (10-10)}{\text{Number of matches}} = 0$$

Referring now to FIG. 8B assume the list of differences is (5, 5, 5, 5, 5, 15, 15, 15, 15)

The median here is 5 and to evaluate the quality of the relationship one computes $$\frac{\left(\begin{array}{c}(5-5) + (5-5) + (5-5) + (5-5) + \\ (5-5) + (15-5) + (15-5) + (15-5) + (15-5)\end{array}\right)}{(9)} = \frac{40}{9} = 4\frac{4}{9}$$

The deviation in this value from zero indicates gaps in the alignment between the sequences D and Q being evaluated. In the preferred embodiment, when comparing genomic sequences to genomic sequences, or when comparing cDNAs to cDNAs, this value is expected to be no more than 3. However in the preferred embodiment the default maximum acceptable value is 25.

Figure 9:
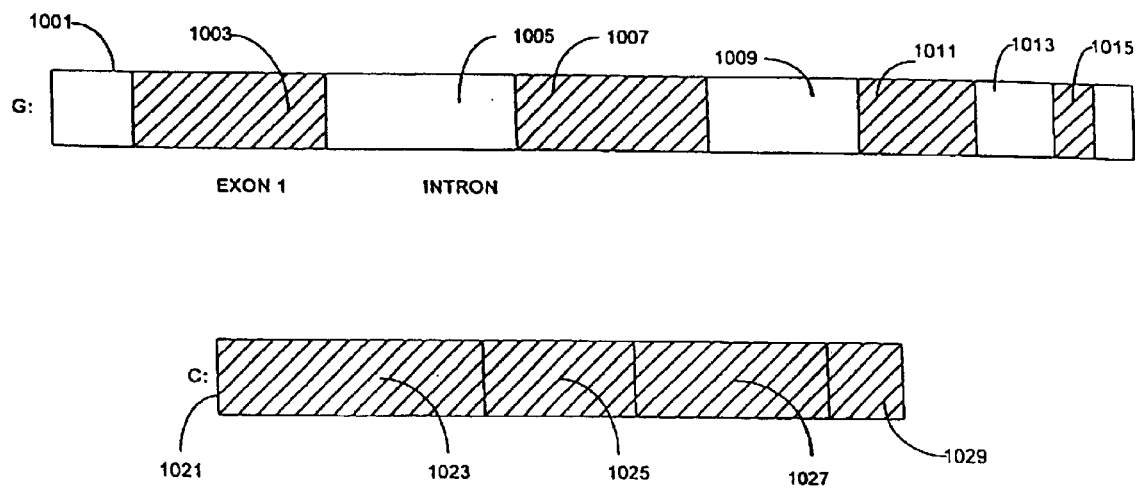
FIG. 9 illustrates exemplary sequences with and without introns.

The previous measures of near identity do not work when there are large gaps such as expected when comparing cDNA sequences with genomic sequences. For example, there are several processing steps that occur while translating the information in genomic DNA into cDNA and finally into protein. During this process introns are removed from the genomic sequence to get to the cDNA. Referring now to FIG. 9 a genomic sequence G 1001 is shown which contains exons 1003, 1007, 1011 and 1015 and introns 1005, 1009 and 1013. (An exon is a region of DNA that encodes a portion of a protein, whereas an intron is a region of DNA that does not encodes a portion of a protein). The introns 1005, 1009 and 1013 are removed to produce the cDNA sequence C 1021. The exons 1003, 1007, 1011 and 1015 from G 1001 should match perfectly the corresponding regions 1023, 1025, 1027 and 1029 in C 1021. Introns are often up to 1,000 nucleotides in length and may be over 100,000 nucleotides long. In such a case, matches between cDNAs and a genomic sequence will fail either of the previous measures since the match density could be low and since there are likely to be many long gaps. In such a case, one can consider just the relative order, or rank, of the tags in Q and D and ignore the absolute position of the tags. The rank correlation coefficient $$r_s = 1 - \frac{6\left(\sum_{i=1}^{m} d_i^2\right)}{m(m-1)}$$

where $d_i$ is the difference in rank of the tags, and where m is the number of tag matches. For example, if the Qtag in rank order 1 of the Qtags matches the Dtag in rank order 3 of the Dtags, the difference in rank of the matching tags d would be 3−1=2. The tag orders agree perfectly when $r_s=1$ and are in opposite order when $r_s=-1$. Probability values for $r_s$ are given in standard statistical tables. A value of $r_s$ near 1 indicates that the tags Q and D have in common appear in nearly the same order, but indicates nothing about the relative distance between the tags. This measure will be useful in locating regions of near identity between cDNAs and a genomic sequence. In a preferred embodiment, near identities are defined as $r_s>0.75$ that is, the minimum acceptable value default is 0.75.

Initially, in a preferred embodiment, a unique genomic DNA database is created by applying the above system to all available human genomic DNA sequence data. As indicated above, in a preferred embodiment, the program ASIDE (A Sequence IDentity Enumerator) is used to enumerate regions of near identity of successive sequences by first scanning the DNA sequences and computing the tags. This is the tag array construction phase. The sequence searching phase is performed by reading back the DNA file as a query file and comparing it against the tag array from Phase I. Phase II compares each DNA sequence from the query set with the tag array to identify all DNA sequences from the database file that contain a region of near identity to the DNA query sequence The DNA sequences are sorted by length. The first (longest) DNA sequence is assigned the identifier Z0 and it is noted that this sequence has been used. (Initially, the mark associated with each DNA sequence is set to 0. This mark is then set to 1 when it is used, that is, assigned to a cluster). Every sequence that is nearly identical to a region of Z0 is added to the Z0 cluster and it is noted that the sequence has been used. In this case, "nearly identical" also indicates that the shorter sequence is completely contained in the longer sequence, not just an overlap. For example, referring to FIG. 10, the sequence B 1203 is completely contained in the longer sequence A 1201 whereas sequence C 1205 is not. On completion of the scanning process, the next (longest unmarked) DNA sequence is assigned Z1 and all sequences that are contained within Z1 are added to the Z1-cluster. This process is repeated until all DNA sequences have been marked. Each Z-cluster represents one entry in the initial unique human genomic DNA database. The position of each member of a cluster relative to the longest sequence in the cluster is maintained. This information allows position specific annotations applied to any member of the cluster to be properly transferred to other appropriate members of the cluster. As an illustration, the process described above took eight hours to complete on a single SGI™ processor (Model R10000) using about 4 Gb memory.

In a preferred embodiment as new human genomic DNA sequence data is generated, it needs to be added to the unique human genomic DNA database. For example, additions can be made in two processes, a regular (daily) incremental update, and a less regular (monthly) reconciliation. In the daily update, each DNA sequence is added to a Z-cluster if the new DNA sequences is contained in a member of the Z-cluster. If there is no Z-cluster that contains the new DNA sequence, a new Z-cluster is created with the new DNA sequence as its only member. This process is completed by using ASIDE with the unique human genomic database as the "database" and the new genomic sequences as the "query" file.

Consider a new DNA sequence that contains a subsequence that is identical to the longest member of a currently existing Z-cluster. In the daily update process, the new DNA sequence will be put in a new Z-cluster, not added to the previous Z-cluster. Occasionally, in a further preferred embodiment, the initial process described above is applied to the set of Z-clusters. This will merge the new, long Z-clusters with any previous Z-clusters that are contained within the new long Z-cluster.

4. Additional Uses of the Algorithm

A. Assembling ESTs

Another use of the invention described herein is in the assembling of ESTs. Expressed Sequence Tags (ESTs) are short (typically 300–750 base pair) fragments of cDNA. These fragments may be located at many positions along the cDNA and will often overlap with one another. The ESTs may be assembled by noticing overlapping regions between ESTs. Assembling ESTs provides at least two benefits. First, the length of the DNA sequence is increased allowing more accurate analysis of the gene. Second, the redundancy and size of the EST database is greatly reduced as the ESTs are assembled.

The first step in assembling an EST database is to find all regions of identity between ESTs in the database. The invention described herein allows the regions of identity between ESTs to be identified very quickly. The second step is to produce an "alignment" of the members for each cluster.

This concept of "alignment" is described as follows: consider the following set of EST sequences

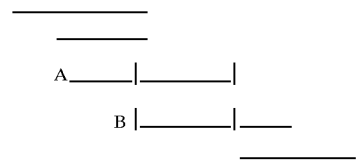

In the above, ESTs A and B are nearly identical in the region defined by the vertical bars. By aligning the ESTs A and B this way, we now have the following, better, picture of the original cDNA from which the ESTs were generated, ———— A only ——|——— A + B ————|—— B only—— wherein the assembled EST is longer than either of the constituent ESTs. This assembled EST is conceptually a mathematical union of the elements of sequences A and B. By continuing this alignment process we can assemble the ESTs into a reasonable approximation of the full cDNA from which these ESTs were generated.

The invention described herein produces a rough alignment that could be used to nearly eliminate the time required to produce the final alignment.

Accordingly, the present invention provides a method for assembling two EST sequences into a single sequence, which is a mathematical union of the elements of the two ESTs, comprising the steps of:

providing a data file containing available EST sequences;

providing a query file containing the available EST sequences;

comparing sequences from the query file to sequences from the data file to determine near identities in respective data and query sequences, designating the respective data and query sequences which contain a near identity as a matched pair; and when a matched pair is found, forming a single sequence designated an assembled EST, which is a mathematical union of the elements of the two ESTs in the matched pair, whereby this assembled EST can replace the matched pair on the data file.

In one embodiment, the comparing and forming steps are repeated until all possible matched pairs of ESTs are determined and their assembled ESTs are created and placed on the data file.

The step of comparing sequences from the data and query files can comprise the steps of:

generating a Dtag file for sequences on the data file;

generating a Qtag file for sequences on the query file; and comparing each tag on the Qtag file to each tag on the Dtag file to determine near identities in the sequences represented by the tags.

The present invention also provides a system for assembling two EST sequences into a single sequence, which is a mathematical union of the elements of the two ESTs, comprising:

a computer system, having a processor, memory, external data storage, input/output mechanisms, a display;

a data file in the computer system containing available EST sequences;

a query file in the computer system containing the available EST sequences;

logic mechanisms in the computer system for comparing sequences from the query file to sequences from the data file to determine near identities in respective data and query sequences, designating the respective data and query sequences which contain a near identity as a matched pair; and when a matched pair is found, forming a single sequence designated an assembled EST, which is a mathematical union of the elements of the two ESTs in the matched pair, whereby this assembled EST can replace the matched pair on the data file.

In one embodiment, the comparing and forming operations are repeated until all possible matched pairs of ESTs are determined and their assembled ESTs are created and placed on the data file.

In a system for assembling two EST sequences into a single sequence, the logic mechanism for comparing sequences from the data and query files can comprise:

a Dtag file generated from sequences on the data file;

a Qtag file generated from sequences on the query file; and a logic mechanism for comparing each tag on the Qtag file to each tag on the Dtag file to determine near identities in the sequences represented by the tags.

B. Mapping ESTs and cDNA Molecules onto Genomic Sequences

Associating cDNAs (e.g., ESTs, assembled ESTs and full length cDNAs) with genomic sequence provides information that cannot be gained from either alone. The genomic sequence contains information that codes for proteins although the information is not continuous. The information is arranged as exons separated by introns. The exons are spliced together (removing the introns) to create a message that can be directly translated into protein. Identifying the exons in genomic sequence and assembling them is only moderately understood and is often done incorrectly. EST and cDNA sequence data are generated after the cellular machinery has properly spliced together the exons and therefore usually correctly code for a protein. Unfortunately, EST data is nearly always incomplete and the cDNA data is often incomplete. The genomic data has the complete information although not spliced. The ESTs and cDNA data have the properly spliced data and are often incomplete. Placing ESTs, assembled ESTs, and cDNAs on the genomic sequence allows one to merge this information to find complete, properly spliced, genes.

The program that is based on the invention presented here can accept a set of "data" sequences and a separate set of "query" sequences. Using the unique human genomic database constructed above as the source of "data" sequences and all primate sequences from genbank (a standard collection of cDNA and other sequences) as the "query" sequences, the program will place each matching query on the genomic sequence that it was generated from (if it is available). Since the cDNAs will not contain the introns, the definition of identity in this process must allow for large gaps in the cDNA sequence when aligned with the genomic sequences. The rank correlation coefficient discussed above provides a good measure of identity while allowing for many large gaps in the alignment. For example, the program was run with 393274083bases in a primate cDNA dataset, and 1286569737 bases in the unique genomic dataset The results identified 112390 genomic/cDNA pairs with regions of identity in 159 minutes using a single SGI™ processor and about 2 Gb of memory.

Accordingly, the present invention provides a method for mapping EST sequences, assembled EST sequences and cDNA sequences onto genomic sequences, comprising the steps of:

providing a data file containing a unique human genomic database;

providing a query file containing primate sequences from available sources including EST sequences, assembled EST sequences and cDNA sequences;

comparing sequences from the query file to sequences from the data file to determine near identities in respective data and query sequences, designating the respective data and query sequences which contain a near identity as a matched pair, and when a matched pair is found, placing each matched query sequence on a data sequence designated by the matched pair, the data sequence designated by the matched pair being the genomic sequence from which the query sequence was generated.

In one embodiment, the step of comparing sequences from the query file to sequences from the data file to determine near identities in respective data and query sequences is done using a rank correlation coefficient of the sequences calculated as follows:

$$r_s = 1 - \frac{6\left(\sum_{i=1}^{m} d_i^2\right)}{m(m-1)}$$

where r is the rank correlation coefficient for a pair of sequences, $d_i$ is a difference in rank of the tags, and m is a number of tag matches, and wherein sequences of near identity are indicated when the rank correlation coefficient for a pair of sequences is less than an indicator value. For example, a suitable indicator value is 0.75.

The present invention also provides a system for mapping EST sequences, assembled EST sequences and cDNA sequences onto genomic sequences, comprising:

a computer system, having a processor, memory, external data storage, input/output mechanisms, a display;

a data file in the computer system containing a unique human genomic database;

a query file in the computer system containing primate sequences from available sources including EST sequences, assembled EST sequences and cDNA sequences;

a logic mechanism in the computer system for comparing sequences from the query file to sequences from the data file to determine near identities in respective data and query sequences, designating the respective data and query sequences which contain a near identity as a matched pair; and when a matched pair is found, placing each matched query sequence on a data sequence designated by the matched pair, the data sequence designated by the matched pair being the genomic sequence from which the query sequence was generated.

In one embodiment, the logic mechanism for comparing sequences from the query file to sequences from the data file to determine near identities in respective data and query sequences, is done using a rank correlation coefficient of the sequences calculated as follows:

$$r_s = 1 - \frac{6\left(\sum_{i=1}^{m} d_i^2\right)}{m(m-1)}$$

where r is the rank correlation coefficient for a pair of sequences, $d_i$ is a difference in rank of the tags, and m is a number of tag matches, and wherein sequences of near identity are indicated when the rank correlation coefficient for a pair of sequences is less than an indicator value. As an illustration, a suitable indicator value is 0.75.

C. Detection of Alternately Spliced cDNA Molecules

The process of splicing together exons from genomic sequence may occur in more than one way resulting in alternately spliced cDNAs. Identifying these alternately spliced cDNAs is important when characterizing a gene and its protein products. Alternately spliced cDNAs may be identified by noticing pairs of cDNAs that contain regions of identity separated by gaps or regions of low similarity.

The method described here can be used to compare a set of cDNAs with itself to locate regions of identity. By using the rank correlation coefficient, pairs of cDNAs that contain regions of near identity and may also have large gaps or regions of low similarity will be enumerated. The alignments generated between each pair of cDNAs containing regions of near identified may be examined to determine if the cDNAs are likely alternate splices of the same gene.

Thus, the present invention provides a method for identifying two cDNA sequences as alternate splices of the same gene, comprising the steps of:

providing a data file comprising a set of cDNA sequences, wherein the cDNA sequences were produced by splicing together exons from a genomic sequence;

providing a query file comprising a copy of the data file;

comparing sequences from the query file to sequences from the data file to determine near identities in respective data and query sequences, designating the respective data and query sequences which contain a near identity as a matched pair; and when a matched pair is found, identifying the matched pair of cDNA sequences as likely alternate splices of the same gene.

In one embodiment, the step of comparing sequences from the query file to sequences from the data file to determine near identities in respective data and query sequences is done using a rank correlation coefficient of the sequences calculated as follows:

$$r_s = 1 - \frac{6\left(\sum_{i=1}^{m} d_i^2\right)}{m(m^2-1)}$$

where r is the rank correlation coefficient for a pair of sequences, $d_i$ is a difference in rank of the tags, and m is a number of tag matches, and wherein sequences of near identity are indicated when the rank correlation coefficient for a pair of sequences is less than an indicator value. As an illustration, the indicator value can be 0.75.

The present invention also provides a system for identifying two cDNA sequences as alternate splices of the same gene, comprising:

a computer system, having a processor, memory, external data storage, input/output mechanisms, a display;

a data file in the computer system comprising a set of cDNA sequences, wherein the cDNA sequences were produced by splicing together exons from a genomic sequence;

a query file in the computer system comprising a copy of the data file;

a logic mechanism in the computer system for comparing sequences from the query file to sequences from the data file to determine near identities in respective data and query sequences, designating the respective data and query sequences which contain a near identity as a matched pair; and when a matched pair is found, identifying the matched pair of cDNA sequences as likely alternate splices of the same gene.

In one embodiment, the logic mechanism for comparing sequences from the query file to sequences from the data file to determine near identities in respective data and query sequences is done using a rank correlation coefficient of the sequences calculated as follows:

$$r_s = 1 - \frac{6\left(\sum_{i=1}^{m} d_i^2\right)}{m(m^2-1)}$$

where r is the rank correlation coefficient for a pair of sequences, $d_i$ is a difference in rank of the tags, and m is a number of tag matches, and wherein sequences of near identity are indicated when the rank correlation coefficient for a pair of sequences is less than an indicator value. As an illustration, the indicator value can be 0.75.

D. SNP Detection

A single nucleotide polymorphism (SNP) is an alteration in a single nucleotide base within a DNA sequence, which differs between individuals. Such genetic variation between human beings may predispose some to disease, and explain why some respond better to certain drugs. SNPs may be useful in tailoring medical treatment to individuals. Given many genomic fragments from many individuals, the methods presented here can identify the fragments from different individuals that are from the same region of the genome since they will be nearly identical. The alignment between the analogous genomic fragments from two individuals will contain some differences and be indicated by tags that are not shared between the two genomic fragments. These missing tags can be examined to determine the SNP that prevented the match.

E. Syntenic Region Alignment

Analogous regions in the genomes of two distinct species are called syntenic. Syntenic regions of the human and mouse genomes (and even the human and fly genomes) can contain remarkably similar DNA. While the methods presented here may produce a rough alignment of syntenic regions, the real value is in anchoring regions of the alignment and therefor greatly reducing the time required to produce a fine alignment.

Having described the invention in terms of a preferred embodiment, it will be recognized by those skilled in the art that various types of general purpose computer hardware may be substituted for the configuration described above to achieve an equivalent result. Similarly, it will be appreciated that arithmetic logic circuits are configured to perform each required means in the claims for performing the various features of sequence recognition, tag value creation, data storage and comparisons and calculations necessary for such comparisons of sequence fragments and or tag files. It will be apparent to those skilled in the art that modifications and variations of the preferred embodiment are possible, such as using different target data domains of combinations of DNA sequence files, cDNA files, EST files, etc, and various combinations thereof as well as using any number of computer processors from IBM, Sun Microsystems, Inc., HP, Apple, SGI, etc., and various operating systems for these platforms, all of which fall within the true spirit and scope of the invention as measured by the following claims.

I claim:

1. In a computer system, a method for finding near identities in a DNA database, the method comprising the steps of:
   providing a first database and a second database;
   generating for the first database a first tag array and for the second database a second tag array; and
   comparing the first tag array to the second tag array using a comparison model to determine areas of the first database which match areas of the second database.

2. The method of claim 1, wherein the first database is a genomic DNA sequence database and the second database is a genomic DNA sequence database.

3. The method of claim 1, wherein the first database is a genomic DNA sequence database and the second database is a cDNA sequence database.

4. The method of claim 1, wherein the first database is a cDNA sequence database and the second database is a cDNA sequence database.

5. The method of claim 1, wherein the step of generating for the first database a first tag array and for the second database a second tag array further comprises steps of generating a tag record which contains a tag value, a value representing a sequence ID of a sequence from which the tag value was generated and a value representing a position on a sequence from which the tag value was generated and storing the tag record in an appropriate tag array.

6. The method of claim 5, wherein the tag value is computed as $$T = \sum_{i=1}^{|DNA|} I(DNA_i) \cdot 4^{(i-1)} \bmod P$$

where T is the tag value
   DNA is a fragment of a DNA sequence,
   |DNA| is a length of the DNA fragment,
   P is a prime number such that P·4 can be stored in one computer word and where $I(DNA_i)$ evaluates to 0, 1, 2, and 3 when $DNA_i$ is A, C, G, and T respectively.

7. The method of claim 1, wherein the step of comparing the first tag array to the second tag array using a comparison model to determine areas of the first database which match areas of the second database further comprises steps of sorting the first tag array on tag value to produce a sorted first tag array, and sorting the second tag array on tag value to produce a sorted second tag array.

8. The method of claim 7, further comprising steps of comparing each tag of each sequence of length l from the sorted first tag array to tags in the sorted second tag array and for those tag values that are equal, recording the tag values and their respective sequence ID and tag position on the sequence values in a matched tag array.

9. The method of claim 8, further comprising steps of using the matched tag array to calculate a match density value for a sequence, where the match density is equal to a total number of tags for the sequence in the matched tag array divided by a total number of tags for the sequence in the sorted second tag array, and using the match density to indicate sequences of near identity when the match density is greater than an indicator value.

10. The method of claim 9, wherein the indicator value is 0.9.

11. The method of claim 8, further comprising steps of using the matched tag array to calculate a mean difference offset value for a pair of sequences; wherein a set of offsets are differences between sequence positions associated with pairs of matching tags, and wherein a median offset is a median value of the set of offsets, and wherein a set of differences comprises differences between the median value and each of the offsets, and wherein a mean difference offset value is a mean value of the set of differences, whereby sequences of near identity are indicated when the mean difference offset value is less than an indicator value.

12. The method of claim 11, wherein the indicator value is 25.

13. The method of claim 11, further comprising steps of using the matched tag array to calculate a rank correlation coefficient for a pair of sequences, wherein the rank correlation coefficient is computed as $$r_s = 1 - \frac{6\left(\sum_{i=1}^{m} d_i^2\right)}{m(m^2 - 1)}$$

where r is the rank correlation coefficient for a pair of sequences,
   $d_i$ is a difference in rank of the tags, and
   m is a number of tag matches, and
wherein sequences of near identity are indicated when the rank correlation coefficient for a pair of sequences is less than an indicator value.

14. The method of claim 13, wherein the indicator value is 0.75.

15. A computer system, having a processor, memory, external data storage, input/output mechanisms, a display, for finding near identities in a DNA database, comprising:
   a first database and a second database;
   logic mechanisms in the computer for generating for the first database a first tag array and for the second database a second tag array; and a comparing mechanism in the computer for comparing the first tag array to the second tag array using a comparison model to determine areas of the first database which match areas of the second database.

16. The computer system of claim 15, wherein the first database is a genomic DNA sequence database and the second database is a genomic DNA sequence database.

17. The computer system of claim 15, wherein the first database is a cDNA sequence database and the second database is a cDNA sequence database.

18. The computer system of claim 15, wherein the first database is a genomic DNA sequence database and the second database is a cDNA sequence database.

19. The computer system of claim 15, wherein the logic mechanisms for generating for the first database a first tag array and for the second database a second tag array further comprises logic mechanisms for generating a tag record which contains a tag value, a value representing a sequence ID of a sequence from which the tag value was generated and a value representing a position on a sequence from which the tag value was generated and a logic mechanism for storing the tag record in an appropriate tag array.

20. The computer system of claim 19, wherein the tag value is computed as $$T = \sum_{i=1}^{|DNA|} I(DNA_i) \cdot 4^{(i-1)} \bmod P$$

where T is the tag value
DNA is a fragment of a DNA sequence,
|DNA| is a length of the DNA fragment,
P is a prime number such that P·4 can be stored in one computer word and where $I(DNA_i)$ evaluates to 0, 1, 2, and 3 when $DNA_i$ is A, C, G, and T respectively.

21. The computer system of claim 15, wherein the comparing mechanism for comparing the first tag array to the second tag array using a comparison model to determine areas of the first database which match areas of the second database further comprises logic mechanisms for sorting the first tag array on tag value to produce a sorted first tag array, and for sorting the second tag array on tag value to produce a sorted second tag array.

22. The computer system of claim 21, further comprising logic mechanisms for comparing each tag of each sequence of length l from the sorted first tag array to tags in the sorted second tag array and for those tag values that are equal, recording the tag values and their respective, sequence ID and tag position on the sequence values in a matched tag array.

23. The computer system of claim 22, further comprising a logic mechanism for using the matched tag array to calculate a match density value for a sequence, where the match density is equal to a total number of tags for the sequence in the matched tag array divided by a total number of tags for the sequence in the sorted second tag array, and using the match density to indicate sequences of near identity when the match density is greater than an indicator value.

24. The computer system of claim 23, wherein the indicator value is 0.9.

25. The computer system of claim 22, further comprising a logic mechanism for using the matched tag array to calculate a mean difference offset value for a pair of sequences; wherein a set of offsets are differences between sequence positions associated with pairs of matching tags, and wherein a median offset is a median value of the set of offsets, and wherein a set of differences comprises differences between the median value and each of the offsets, and wherein a mean difference offset value is a mean value of the set of differences, whereby sequences of near identity are indicated when the mean difference offset value is less than an indicator value.

26. The computer system of claim 25, wherein the indicator value is 25.

27. The computer system of claim 22, further comprising a logic mechanism for using the matched tag array to calculate a rank correlation coefficient for a pair of sequences, wherein the rank correlation coefficient is computed as $$r_s = 1 - \frac{6\left(\sum_{i=1}^{m} d_i^2\right)}{m(m^2 - 1)}$$

where r is the rank correlation coefficient for a pair of sequences, $d_i$ is a difference in rank of the tags, and m is a number of tag matches, and wherein sequences of near identity are indicated when the rank correlation coefficient for a pair of sequences is less than an indicator value.

28. The computer system of claim 28, wherein the indicator value is 0.75.

29. A computer program product stored on a computer readable medium for finding near identities in a DNA sequence database, comprising:

a first code mechanism for comparing a DNA sequence on a query database to DNA sequences on a data database, wherein a tag array (designated as Qtags) is generated for each of the DNA sequences on the query database and wherein a tag array (designated Dtags) is generated for each of the DNA sequences on the data database; and a second code mechanism for comparing each Qtag to each Dtag, using a comparison model, wherein near identities of sequences in the two databases are identified.

30. The computer program product of claim 29, further comprising a code mechanism for using data which indicate that two sequences contain near identities for purposes of creating a unique DNA genome database.

31. The computer program product of claim 29, further comprising a code mechanism for using data which indicate that two sequences contain near identities for purposes of assembling two EST sequences containing near identities (a matched pair) into a single sequence (an assembled EST) which is a mathematical union of the elements of the two ESTs in the matched pair, whereby this assembled EST can replace the matched pair on the data file.

32. The computer program product of claim 29, further comprising a code mechanism for using data which indicate that two sequences contain near identities for purposes of mapping EST sequences, assembled EST sequences and cDNA sequences onto genomic sequences.

33. The computer program product of claim 32, further comprising a code mechanism for comparing sequences from the query file to sequences from the data file to determine near identities in respective data and query sequences by using a rank correlation coefficient of the sequences calculated as follows:

$$r_s = 1 - \frac{6\left(\sum_{i=1}^{m} d_i^2\right)}{m(m^2 - 1)}$$

where r is the rank correlation coefficient for a pair of sequences, d$_i$ is a difference in rank of the tags, and m is a number of tag matches, and wherein sequences of near identity are indicated when the rank correlation coefficient for a pair of sequences is less than an indicator value.

34. The computer program product of claim 33, wherein the indicator value is 0.75.

35. The computer program product of claim 29, further comprising a code mechanism for using data which indicate that two sequences contain near identities for purposes of identifying two cDNA sequences as likely alternate splices of the same gene.

* * * * *

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Illustrative nucleotide sequence

<400> SEQUENCE: 1
actgagctac tctgccactc ttctactgga cc                               32

<210> SEQ ID NO 2
<211> LENGTH: 33
<212> TYPE: DNA
<213> ORGANISM: Artificial Sequence
<220> FEATURE:
<223> OTHER INFORMATION: Illustrative nucleotide sequence

<400> SEQUENCE: 2
ctgagctact ctgccactct tctactggac ctg                              33

<210> SEQ ID NO 3
<211> LENGTH: 50
<212> TYPE: DNA
<213> ORGANISM: Artificial Sequence
<220> FEATURE:
<223> OTHER INFORMATION: Illustrative nucleotide sequence

<400> SEQUENCE: 3
ctgagctact ctgccactct tctactggac ctggtcaact agccagcatg            50

<210> SEQ ID NO 4
<211> LENGTH: 10
<212> TYPE: DNA
<213> ORGANISM: Artificial Sequence
<220> FEATURE:
<223> OTHER INFORMATION: Illustrative nucleotide sequence

<400> SEQUENCE: 4
gcaattgctt                                                        10

<210> SEQ ID NO 5
<211> LENGTH: 13
<212> TYPE: DNA
<213> ORGANISM: Artificial Sequence
<220> FEATURE:
<223> OTHER INFORMATION: Illustrative nucleotide sequence
<220> FEATURE:
```

<221> NAME/KEY: misc_feature
<222> LOCATION: (1)...(13)
<223> OTHER INFORMATION: n = an unlimited number of any nucleotide

<400> SEQUENCE: 5
ctcgaaatng gtc                                                           13

<210> SEQ ID NO 6
<211> LENGTH: 17
<212> TYPE: DNA
<213> ORGANISM: Artificial Sequence
<220> FEATURE:
<223> OTHER INFORMATION: Illustrative nucleotide sequence
<220> FEATURE:
<221> NAME/KEY: misc_feature
<222> LOCATION: (1)...(17)
<223> OTHER INFORMATION: n = an unlimited number of any nucleotide

<400> SEQUENCE: 6
natcatcatc atcatcn                                                       17

<210> SEQ ID NO 7
<211> LENGTH: 14
<212> TYPE: DNA
<213> ORGANISM: Artificial Sequence
<220> FEATURE:
<223> OTHER INFORMATION: Illustrative nucleotide sequence
<220> FEATURE:
<221> NAME/KEY: misc_feature
<222> LOCATION: (1)...(14)
<223> OTHER INFORMATION: n = an unlimited number of any nucleotide

<400> SEQUENCE: 7
ngagagagag agan                                                          14

<210> SEQ ID NO 8
<211> LENGTH: 22
<212> TYPE: DNA
<213> ORGANISM: Artificial Sequence
<220> FEATURE:
<223> OTHER INFORMATION: Illustrative nucleotide sequence
<220> FEATURE:
<221> NAME/KEY: misc_feature
<222> LOCATION: (1)...(22)
<223> OTHER INFORMATION: n = an unlimited number of any nucleotide

<400> SEQUENCE: 8
nagctagcta gctagctagc tn                                                 22

<210> SEQ ID NO 9
<211> LENGTH: 771
<212> TYPE: DNA
<213> ORGANISM: Artificial Sequence
<220> FEATURE:
<223> OTHER INFORMATION: Illustrative nucleotide sequence
<220> FEATURE:
<221> NAME/KEY: misc_feature
<222> LOCATION: (1)...(771)
<223> OTHER INFORMATION: n = an unlimited number of any nucleotide

<400> SEQUENCE: 9
agcgtgtgtc agtgcgaaaa ccccgagata agctatcacg taatcgccaa gtgtcgttaa        60
attcaccata gttcacattt taaataccac gtatcatgta taaattaaac attgggcccc       120
tccactgagg tacgtgtgta gcgcttagtg ggcgacacgc atgggcgcaa gcaggaaaag       180
tttaaaaaga aggccgccct tagtgtcacc cgacaaagcc aaagcctgac aaaccccgaa       240
ttgcactcgc aattcacggc atacggtcat ttagcggtct atcaccgtag tggtatattg       300

-continued

```
taatccatcg atacggcgtt tggtttgtct tacggttagt aaggggcgtg cggacgatat    360
taggtgcaaa gtcttcaagc atcacaccag aaaagttacc aaggttgtcg cgtgaaaagt    420
taccaagcct cacacgtgaa aagttaccaa tcctgtcgcg tgaaaagtta ccaagcatca    480
cacgtgaaaa gttaccaatc atgtcgcgtg aaaagttacc aagcatcaca cgtgaaaagt    540
taccaatcat gtcgcgtgaa aagttaccaa gcatcacacg tgaaaagtta ccaatcattg    600
cgcgtgaaaa gttaccaagc aactcgcgtg aaaagttacc aagcatcatt acactttctc    660
ttacaaagaa tttaagaaaa tcgttccacc ccgccatcca tcatcttcaa acctcgcttt    720
gccccgggca ctcgtattat gcgggtggcg ggctcgcggc acaagagagc n             771
```